United States Patent
Hyun et al.

(10) Patent No.: US 10,758,646 B2
(45) Date of Patent: Sep. 1, 2020

(54) PREPARING METHOD OF NERVE CONDUITS INCLUDING CELLS

(71) Applicant: Wiregene Co., Ltd., Chungcheongnam-do (KR)

(72) Inventors: Jung Keun Hyun, Chungcheongnam-do (KR); Jong-Wan Kim, Chungcheongnam-do (KR); Young-Jin Son, Blue Bell, PA (US); Min Soo Kim, Chungcheongnam-do (KR); Hong Sun Ahn, Chungcheongnam-do (KR)

(73) Assignee: Wiregene Co., Ltd., Chungcheongnam-do (KR)

( * ) Notice: Subject to any disclaimer, the term of this patent is extended or adjusted under 35 U.S.C. 154(b) by 136 days.

(21) Appl. No.: 15/797,063

(22) Filed: Oct. 30, 2017

(65) Prior Publication Data
US 2018/0126041 A1    May 10, 2018

(30) Foreign Application Priority Data

Nov. 4, 2016   (KR) ......................... 10-2016-0146706
Oct. 26, 2017  (KR) ......................... 10-2017-0140473

(51) Int. Cl.
*A61L 27/56*    (2006.01)
*A61L 27/58*    (2006.01)
(Continued)

(52) U.S. Cl.
CPC ............ *A61L 27/56* (2013.01); *A61F 2/0077* (2013.01); *A61F 2/02* (2013.01); *A61L 27/18* (2013.01); *A61L 27/3604* (2013.01); *A61L 27/3675* (2013.01); *A61L 27/383* (2013.01); *A61L 27/58* (2013.01); *C08J 9/26* (2013.01); *C08J 9/28* (2013.01); *A61B 17/1128* (2013.01); *A61F 2002/0081* (2013.01);
(Continued)

(58) Field of Classification Search
CPC ............ A61B 17/1128; A61L 2430/32; A61L 2430/38; A61L 2400/08; A61L 27/18; A61L 27/58; A61L 27/383; A61L 27/56; A61L 27/3675; A61L 27/3604; A61F 2002/0081; A61F 2002/0086; A61F 2/0077; A61F 2/02; C08J 2207/10; C08J 2201/044; C08J 2201/0544; C08J 2367/04; C08J 2205/044; C08J 2205/06; C08J 9/26; C08J 9/28; C08L 67/04
See application file for complete search history.

(56) References Cited

FOREIGN PATENT DOCUMENTS

KR    10-2015-0105826       9/2015

OTHER PUBLICATIONS

Schwann cell-seeded scaffold with longitunially oriented microchannels for reconstruction of sciatic nerve in rats. Zhang YG, Sheng QS, Qi FS, Hu XY, Zhao W, Lan Lf, Huang JH, Luo ZJ . 2013. J Mater Sci: Mater Med. Springer. 24: pp. 1767-1780. (Year: 2013).*

* cited by examiner

*Primary Examiner* — Christine H Matthews
*Assistant Examiner* — Joshua Daryl D Lannu

(57) ABSTRACT

The present invention relates to a method for preparing a nerve conduit containing cells, more particularly to a method for preparing a porous nerve conduit containing cells, having micropores formed in microchannels, wherein the nerve conduit containing cells prepared according to the present invention can be usefully used in in-vitro and in-vivo researches on nerves.

14 Claims, 16 Drawing Sheets

(51) Int. Cl.
*A61L 27/18* (2006.01)
*C08J 9/26* (2006.01)
*C08J 9/28* (2006.01)
*A61L 27/36* (2006.01)
*A61F 2/00* (2006.01)
*A61F 2/02* (2006.01)
*A61L 27/38* (2006.01)
*A61B 17/11* (2006.01)

(52) U.S. Cl.
CPC ... *A61F 2002/0086* (2013.01); *A61L 2400/08* (2013.01); *A61L 2430/32* (2013.01); *A61L 2430/38* (2013.01); *C08J 2201/044* (2013.01); *C08J 2201/0544* (2013.01); *C08J 2205/044* (2013.01); *C08J 2205/06* (2013.01); *C08J 2207/10* (2013.01); *C08J 2367/04* (2013.01)

A  Gross images of scaffold for *in vitro* & *in vivo* study

B  PDMS device for *in vivo* experiment

PREPARING METHOD OF NERVE CONDUITS INCLUDING CELLS

CROSS-REFERENCE TO RELATED APPLICATION

This application claims priority of Korean Patent Application No. 10-2016-0146706, filed on Nov. 4, 2016, and priority of Korean Patent Application No. 10-2017-0140473, filed on Oct. 26, 2017, in the KIPO (Korean Intellectual Property Office), the disclosure of which is incorporated herein entirely by reference.

BACKGROUND OF THE INVENTION

Field of the Invention

The present invention relates to a method for preparing a nerve conduit containing cells, more particularly to a method for preparing a porous nerve conduit containing cells, having micropores formed in microchannels.

Description of the Related Art

When a peripheral nerve is damaged due to injury, the sections of the cut nerve are connected with each other directly. However, such anastomosis is almost impossible for most nerves. In this case, autologous nerve grafting is conducted to restore its function. However, the autologous nerve grafting is problematic in that it is difficult to match the thickness and shape of the nerve tissue of the damaged area and the grafted nerve tissue, the nerves that can be taken for the grafting are limited and the decline in function can occur at the area where the grafted nerve is taken. Therefore, a nerve conduit is used to restore the function of a damaged nerve.

The nerve conduit connects both ends of the damaged nerve and serves as a means of guiding nerve regeneration. The both ends of the damaged nerve are fixed inside the nerve conduit to induce the connection of the nerve in the conduit. When the nerve conduit is used, it is advantageous in that the infiltration of scar tissue interfering with nerve regeneration can be prevented, nerve regeneration can be induced along a desired direction, the nerve regeneration promoting substances secreted from the nerve itself is maintained inside the conduit and the substances interfering with the regeneration can be blocked.

The nerve conduit should be biocompatible to avoid tissue rejection and should be biodegraded after nerve regeneration so that the removal of the nerve conduit is unnecessary after the nerve regeneration. Also, the degradation product of the nerve conduit should be nontoxic in the body.

In addition, the nerve conduit should have the mechanical property necessary to maintain the inside space during the nerve regeneration. The nerve conduit should have suitable flexibility and tensile strength so that the end portion of the nerve conduit can be maintained stably after the insertion of the nerve conduit. Also, the nerve conduit should be able to prevent damage to nearby normal tissues and should be easily transplantable.

As the material of the nerve conduit, natural polymers such as collagen, chitosan, etc. and synthetic polymers such as silicone, polylactic acid (PLA), polyglycolic acid (PGA), poly(lactic-co-glycolic acid) (PLGA), polycaprolactone, etc. are available.

Among them, collagen is the most frequently used natural polymer material. Collagen has been frequently used as the material of the nerve conduit for nerve regeneration due to excellent biocompatibility and weak antigenicity. However, the use of collagen is problematic in that it has to be extracted from an animal, storage is complicated and large-scale production is difficult. Also, it costs a lot to prepare the nerve conduit using collagen. In addition, the nerve conduit prepared from collagen is limited in clinical application because of weak tensile strength.

The synthetic polymers such as PLA, PLGA, etc. have been verified to be biocompatible. A nerve conduit based on these synthetic polymers has superior structural stability and tensile strength because is formed as a tube without pores (small holes). However, the synthetic polymer-based nerve conduit is problematic in that control of physical properties is difficult. In addition, the synthetic polymer-based nerve conduit known thus far is disadvantageous in that the exchange of body fluid is not achieved easily.

Korean Patent Application No. 2014-0027854 discloses a method for preparing a synthetic polymer-based nerve conduit using glass fibers. However, the nerve conduit still has the problem that the exchange of body fluid is difficult because it is in the form of a polymer tube without pores.

As described above, the nerve conduit is prepared from a biodegradable material. It is necessary to measure the time required for degradation of the biodegradable material. In general, the biodegradation of the biodegradable nerve conduit prepared from the biomaterial is determined by measuring weight change.

However, the weight of the biomaterial varies greatly depending on the moisture remaining in the material. For a nerve conduit having an internal structure, additional data are required regarding how the initial internal structure is changed as the nerve conduit is degraded. However, such information is not enough.

In order to solve these problems, the inventors of the present invention have researched on a porous nerve conduit having microchannels and micropores at the same time and have completed the present invention. The inventors of the present invention have also researched on a nerve conduit containing cells and have completed the present invention.

SUMMARY OF THE INVENTION

The present invention is directed to providing a method for preparing a porous nerve conduit containing cells.

The present invention is also directed to providing a porous nerve conduit containing cells prepared by the preparation method.

The present invention is also directed to providing a method for regenerating a nerve.

The present invention provides a method for preparing a porous nerve conduit containing cells, including: a) a step of preparing a polymer material for a nerve conduit by dissolving a hydrophobic biocompatible polymer in a water-miscible organic solvent; b) a step of preparing a nerve conduit formed of a porous polymer having micropores formed in microchannels by immersing the polymer material for a nerve conduit in a hydrophilic solution and thereby separating the organic solvent from the polymer material; c) a step of preparing a nerve conduit-inserted device by inserting the nerve conduit in a chamber; d) a step of connecting a pump to the upper portion of the nerve conduit-inserted device via a tube and connecting a medium reservoir containing a culture medium to the lower portion via a tube;

e) a step of adding cells to the culture medium in the medium reservoir; f) a step of seeding the cells into the nerve conduit of the step c) by supplying the culture medium in the medium reservoir of the step e) to the nerve conduit-inserted device using the pump of the step d); and g) a step of culturing the cells by supplying the culture medium in the medium reservoir of the step e) to the cell-seeded nerve conduit of the step f) using the pump of the step d).

The nerve conduit having microchannels may be disposed vertically such that the culture medium flows from the upper end to the lower end of the nerve conduit by gravity.

The porous nerve conduit may be for regeneration of a central nerve or a peripheral nerve.

The nervous system of higher animals is classified into the central nervous system, the peripheral nervous system and the autonomic nervous system. The central nervous system is a nervous system including the brain and the spinal cord. The peripheral nervous system is a nervous system which diverges from the central nervous system such as the brain and spinal cord and is distributed throughout the body like branches.

In general, when the axon of the neuron constituting the peripheral nervous system is physically damaged, it regenerates normally and restores its function with time. However, when the peripheral nerve is damaged due to accidents, surgery, etc., social activities may be severely affected. In particular, when the nerves of the hands or feet are cut, it is difficult to connect them. For the central nervous system, neuronal damage leads to permanent loss of function.

When the peripheral nerve is cut, the cut nerve grows at the peripheral site at a speed of about 1 mm per day. Therefore, the cut nerve can be regenerated by introducing a tube-type nerve conduit to the cut site.

The nerve conduit serves as a passage for connecting the broken nerve tissue and regenerating nerve fibers. Accordingly, when both ends of the cut nerve are connected to the nerve conduit, the nerve may be regenerated as nerve fiber grows at one side of the nerve inside the nerve conduit. In addition, the nerve conduit provides a controlled microenvironment and the growth of axon may be promoted as neurotrophic factors secreted from the damaged nerve are concentrated in the conduit.

It is known that the central nerve such as the spinal cord, etc. cannot be regenerated once it is damaged by injury such as a traffic accident or by cerebrovascular accident, which is contrasted with the peripheral nerve. Because the central nerve cannot be regenerated once it is damaged, the damage to the central nerve often leads to partial or complete paralysis.

The damaged central nerve can be regenerated by using the nerve conduit. An example is as follows. Schwann cells help nerve regeneration. By attaching the Schwann cells to the nerve conduit and connecting the nerve conduit with the Schwann cells attached to the damaged central nerve or peripheral nerve, the regeneration of axon can be facilitated.

Accordingly, the porous nerve conduit containing cells of the present invention allows nerve generation by using the nerve conduit containing cells only without the need of additionally administering cells or drugs that help nerve regeneration. Regeneration of the peripheral nerve or the central nerve is possible by using the nerve conduit containing cells of the present invention.

In the present invention, the term "hydrophobic biocompatible polymer" refers to a polymer which is biocompatible, biodegradable and insoluble in water.

As the hydrophobic biocompatible polymer of the step a), any hydrophobic biocompatible polymer commonly used in the related art may be used without limitation. Specifically, one or more selected from a group comprising of polylactic acid (PLA), poly-L/D-lactide (PLDA), poly-L-lactic acid (PLLA), polyglycolic acid (PGA)), polydioxanone, polyhydroxybutyrate (PHB), polyhydroxyalkanoate (PHA) poly (lactic-co-glycolic acid) (PLGA), polycaprolactone (PCL), a copolymer thereof and a mixture thereof may be used, although not being necessarily limited thereto.

In the present invention, the term "water-miscible organic solvent" refers to an organic solvent which is miscible at least partly with water or completely with water.

As the water-miscible organic solvent of the step a), any water-miscible organic solvent used in the related art may be used without limitation. Specifically, it may be selected from a group comprising of ethanol, isopropyl alcohol, N-methyl-2-pyrrolidone, 2-pyrrolidone, glycerol, propylene glycol, polyethylene glycol, tetraglycol, glycerol formal, ethyl acetate, ethyl lactate, diethyl carbonate, propylene carbonate, acetone, methyl ethyl ketone, dimethyl sulfoxide, dimethyl sulfone, tetrahydrofuran, tetrahydrofurfuryl alcohol, succinic acid diethyl ester, triethyl citrate, dibutyl sebacate, dimethylacetamide, lactic acid butyl ester, propylene glycol diacetate, diethylene glycol monoethyl ether and a mixture thereof, although not being necessarily limited thereto. More specifically, it may be N-methyl-2-pyrrolidone, tetraglycol or dimethyl sulfoxide, although not being necessarily limited thereto.

In an exemplary embodiment of the present invention, a PLGA-TG or PCL-TG solution prepared by using poly (lactic-co-glycolic acid) (PLGA) or polycaprolactone (PCL) as the hydrophobic biocompatible polymer and tetraglycol (TG) as the water-miscible solvent is used as the polymer material. In particular, when the polymer material is prepared by mixing PLGA with TG, it is advantageous in that a process of dissolving the polymer material again can be omitted because a solution state is maintained at room temperature after the PLGA is dissolved with the TG.

By immersing the polymer material for a nerve conduit in the hydrophilic solution and thereby separating the organic solvent from the polymer material, a nerve conduit formed of a porous hydrophobic polymer having micropores may be obtained.

A detailed description is given as follows. When the polymer material for a nerve conduit formed of the hydrophobic biocompatible polymer and the water-miscible organic solvent is immersed in the hydrophilic solution, micropores are formed in the polymer as the organic solvent is released from the polymer, i.e., as the organic solvent is phase-separated.

In the present invention, the hydrophilic solution includes water, although not being limited thereto.

In the present invention, the term "micropore" refers to a very small nano-sized hole. In the present invention, the micropore refers to a very small nano-sized hole with a size of 1 μm or smaller.

The polymer material for a nerve conduit of the step a) may be one in which the hydrophobic biocompatible polymer is dissolved in the water-miscible organic solvent at a concentration of 10-40 weight/volume % (w/v %), specifically 10-25 w/v %, more specifically 15-25 w/v %, most specifically 20 w/v %.

The term "weight/volume % (w/v %)" refers to the weight (g) of the hydrophobic polymer dissolved in 100 mL of the organic solvent.

If the concentration is below 10 w/v %, porosity may increase due to the excessive use of the water-miscible organic solvent. And, if the concentration exceeds 40 w/v %, enough micropores may not be formed.

The nerve conduit formed of a porous polymer having micropores formed in microchannels of the step b) may be prepared by: a step of inserting a plurality of glass fibers into a container having upper and lower channels; a step of injecting a polymer material for a nerve conduit containing a hydrophobic biocompatible polymer and a water-miscible organic solvent into the container in which the plurality of glass fibers are inserted; a step of infiltrating the polymer material between the glass fibers by applying vacuum to the upper channel; a step of separating the glass fibers with the polymer material infiltrated from the container; and a step of dissolving the glass fibers by immersing the separated glass fibers in a hydrophilic solution.

The polymer material for a nerve conduit may be one in which the hydrophobic biocompatible polymer is dissolved in the water-miscible organic solvent at a concentration of 10-40 weight/volume % (w/v %).

And, in the step of dissolving the glass fibers, microchannels may be formed as the hydrophobic biocompatible polymer is cured and micropores may be formed in the microchannels formed of the hydrophobic polymer as the water-miscible organic solvent is mixed with the hydrophilic solution and released from the hydrophobic polymer.

The term "microchannel" refers to a void space with a size of 5-20 μm formed as the glass fibers are dissolved and means a channel with a microstructure formed inside the nerve conduit. The microchannel guides the growth of axons along a desired direction and prevents infiltration of scar tissue which interferes with nerve regeneration. In addition, a structure capable of drug delivery, etc. may be provided by attaching neurotrophic factors, etc. to the microchannels formed inside the nerve conduit.

The nerve conduit of the present invention may have about 1,000-10,000 channels. But, it may also contain more channels.

The present invention provides a method for preparing a porous nerve conduit having micropores formed in microchannels. The processes of forming the microchannels and the micropores are described in detail as follows.

The polymer material for a nerve conduit formed of the hydrophobic biocompatible polymer and the water-miscible organic solvent is infiltrated between the space of the glass fibers filled in the container (e.g., a glass tube). Because the space between the glass fibers is narrow, the polymer material may be infiltrated by using negative pressure or positive pressure. After the polymer material is filled between the glass fibers, the glass fibers and the polymer material are separated from the container and immersed in the hydrophilic solution. Then, microchannels are formed in the space that has been occupied by the glass fibers as the glass fibers are dissolved and micropores are formed as the water-miscible organic solvent is released from the polymer material. Specifically, when the glass fibers are dissolved in the hydrophilic solution (e.g., water) and the water is contacted with the hydrophobic polymer, microchannels are formed as the polymer having hydrophobic property is cured. And, when water is introduced into the newly formed microchannels, micropores are formed as the water-miscible organic solvent is mixed with the water and released from the hydrophobic polymer, i.e., as the organic solvent is phase-separated.

The nerve conduit prepared according to the present invention allows easy body fluid exchange in vivo due to the microchannels having the micropores formed.

The lower channel may have a smaller diameter than the upper channel and the container may be sloped with a discontinuous angle.

Because the lower channel has a smaller diameter than the upper channel, the glass fibers injected into the container may remain filled inside the container without flowing out.

The container may be sloped with a discontinuous angle. More specifically, the container may have the upper and lower channels formed to be sloped with a discontinuous angle.

Due to the container sloped with a discontinuous angle and the upper and lower channels thereof, the glass fibers inserted into the container have constant intervals and the microchannels formed in the space where the glass fibers have been dissolved also have constant intervals. That is to say, because the porous nerve conduit prepared according to the present invention has microchannels formed with constant intervals, nerve regeneration can be induced along the same direction.

The upper channels and the lower channels of the container may be formed by heating the center portion of the glass tube and thereby forming a bottleneck, although not being limited thereto.

The polymer material for a nerve conduit may be in a solution state at room temperature.

In the present invention, the "room temperature" means a temperature of 15-25° C.

The method for preparing a porous nerve conduit containing cells may further include, after the step of dissolving the glass fibers: a step of cooling a nerve conduit formed after the glass fibers are dissolved with liquid nitrogen; and a step of shaping the cooled nerve conduit by cutting.

The container may be formed of a transparent material so that the infiltration of the polymer material for a nerve conduit can be checked visually. Specifically, the transparent material may be glass, although not being necessarily limited thereto.

The application of vacuum may be repeated multiple times. Through this, a nerve conduit with a uniform density may be prepared. The application of vacuum into the container (e.g., a glass tube) may be repeated multiple times using a syringe, although not being necessarily limited thereto.

The chamber of the step c) may be prepared from any polymer that can be shaped using a mold, a 3D printer, etc. without limitation. Specifically, it may be formed of polydimethylsiloxane (PDMS).

In an exemplary embodiment of the present invention, the nerve conduit-inserted device may be prepared by preparing a chamber formed of polydimethylsiloxane (PDMS), inserting the nerve conduit in the chamber, filling the space between the PDMS chamber and the nerve conduit using agarose and then sealing by covering with a cover glass. Because the nerve conduit according to the present invention can be prepared to have various lengths, PDMS devices of various lengths can be prepared accordingly.

Specifically, the cell of the step e) may be a nerve cell, although not being limited thereto.

The nerve cell may be one or more selected from a group comprising of a Schwann cell, an astrocyte and an oligodendrocyte, although not being limited thereto. Specifically, it may be a Schwann cell.

In the present invention, the "Schwann cell" serves to help nerve regeneration. By attaching the Schwann cell to the nerve conduit and connecting the Schwann cell-attached nerve conduit to a damaged peripheral nerve or central nerve, the regeneration of axon can be facilitated.

Specifically, the nerve cell may have a diameter of 10-30 μm similarly to that of the microchannel, i.e., 10-20 μm. If the diameter of the nerve cell is smaller than the diameter of the microchannel, the nerve cell may be discharged out of the nerve conduit along with the incoming culture medium. And, if the diameter of the nerve cell is larger than the diameter of the microchannel, the nerve cell may not be able to enter the microchannel of the nerve conduit.

The flow rate of the culture medium of the step f) or the step g) may be 30-60 µL/min.

If the flow rate is higher than the above range, the cell may be discharged out of the nerve conduit along with the fast incoming culture medium. And, if the flow rate is lower than the above range, the cell may not reach the nerve conduit along the tube.

The nerve conduit-inserted device may allow the seeded cell to grow inside the microchannel in the nerve conduit.

The culture medium for culturing the cell may further contain a nerve-related growth factor or a drug, if necessary. But, there is no problem at all in cell growth or nerve regeneration even when it does not contain a nerve-related growth factor or a drug.

The term "nerve-related growth factor" refers to a factor which affects the growth of the axon, etc. of a nerve cell.

The nerve-related growth factor may be one or more selected from a group including a neurotrophic factor (NTF), although not being limited thereto. The neurotrophic factor may be or may be selected from a group including of NT-3 (neurotrophin-3), NT-4 (neurotrophin-4), BDNF (brain-derived neurotrophic factor), NGF (nerve growth factor), GDNF (glial-derived neurotrophic factor), CNTF (ciliary neurotrophic factor) and a mixture thereof.

The term "drug" refers to any substance that is thought possibly to affect the growth of the axon, etc. of a nerve cell.

The drug may include a chemically synthesized substance, an extract from a natural product or a nucleotide, although not being limited thereto.

In another aspect, the present invention provides a porous nerve conduit containing cells, having micropores formed in microchannels, prepared by the preparation method described above.

The microchannels may be formed along the axis direction of the nerve conduit as the glass fibers are inserted into the container along the axis direction.

The microchannels may be formed as a polymer material for a nerve conduit formed of a water-miscible organic solvent and a hydrophobic biocompatible polymer reacts with a hydrophilic solution and the hydrophobic biocompatible polymer is cured and the micropores may be formed in the microchannels formed of the hydrophobic polymer as the water-miscible organic solvent is mixed with the hydrophilic solution and released from the hydrophobic biocompatible polymer.

In another aspect, the present invention provides a method for regenerating a nerve by transplanting the nerve conduit according to the present invention into a damaged nerve area.

The nerve may be a peripheral nerve or a central nerve.

In an exemplary embodiment of the present invention, after inserting the glass fibers into the upper channels of the container (glass tube) along the axis direction, a polymer material (PLGA-TG solution) is injected into the container and infiltrated into the glass fibers by applying vacuum. Then, after separating the glass fibers from the container, the glass fibers are dissolved completely by immersing in water (DW). When the glass fibers are dissolved, microchannels are formed as the hydrophobic polymer is contacted with water and cured and micropores are formed in the microchannels. That is to say, the nerve conduit having microchannels with micropores formed in the axis direction is formed in the space where the glass fibers have been dissolved by inserting the glass fibers along the axis direction of the container and then dissolving the glass fibers.

In another exemplary embodiment of the present invention, a peripheral nerve can be regenerated using the prepared nerve conduit without having to use additional growth factors, drugs, etc. that help nerve regeneration.

The porous nerve conduit prepared according to the present invention may be prepared to have various diameters and lengths. In addition, the diameter and the length of the nerve conduit of the present invention may be changed as desired when preparing the nerve conduit to be applicable to in-vitro and in-vivo researches on nerves.

The present invention provides the following effects.

According to a preparation method of the present invention, a polymer material in which a hydrophobic biocompatible polymer is dissolved in a water-miscible solvent is infiltrated between glass fibers and then immersed in a hydrophilic solution. Then, microchannels are formed as the hydrophobic polymer is contacted with the hydrophilic solution and cured, whereas micropores are formed in the hydrophobic biocompatible polymer as the water-miscible solvent is released from the polymer. The micropores allow exchange of body fluid.

As the hydrophobic biocompatible polymer is mixed with the water-miscible solvent, the melting point of the polymer solution is lowered. Therefore, after the hydrophobic biocompatible polymer is dissolved in the water-miscible solvent, the solution state is maintained at room temperature and a process of dissolving the polymer material again is unnecessary.

By infiltrating the polymer solution with a predetermined viscosity into the space between the glass fibers and repeatedly applying vacuum multiple times, a nerve conduit with a uniform density can be prepared.

A peripheral nerve and/or a central nerve can be regenerated using the nerve conduit according to the present invention without having to use additional regeneration factors, drugs, etc. that help nerve regeneration.

BRIEF DESCRIPTION OF THE DRAWINGS

The above and other features and advantages will become more apparent to those of ordinary skill in the art by describing in detail exemplary embodiments with reference to the attached drawings, in which.

In the following description, the same or similar elements are labeled with the same or similar reference numbers.

DETAILED DESCRIPTION

Figure 1:
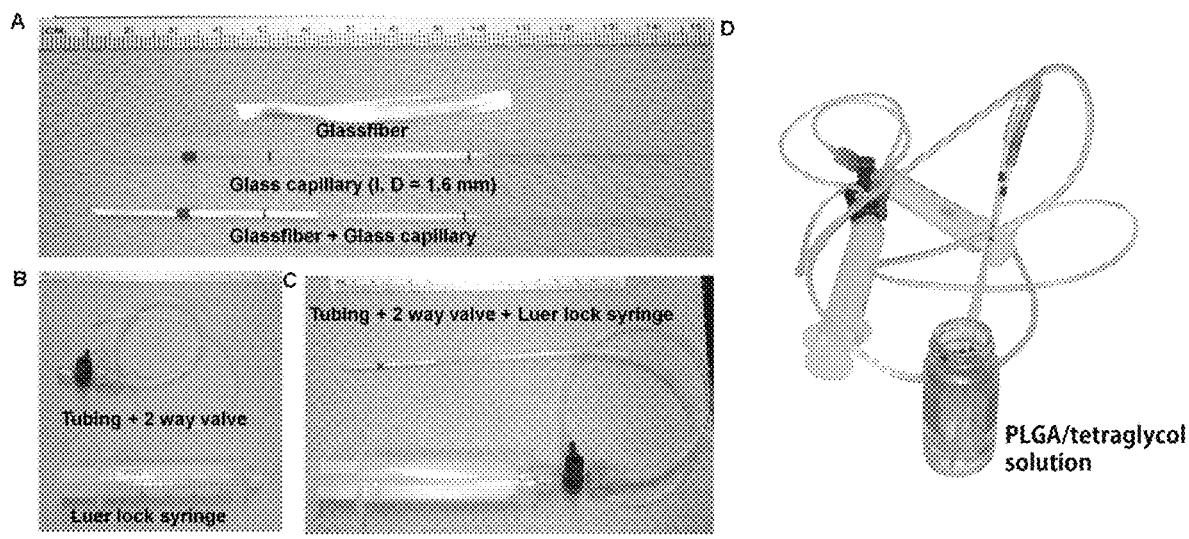
FIG. 1 shows photographs illustrating a method for preparing a porous nerve conduit. A shows glass fibers, a glass capillary and a glass capillary into which glass fibers are inserted, B shows a silicone tube coupled with a 2-way valve and a Luer lock syringe, C shows a silicone tube coupled with a 2-way valve and a Luer lock syringe, and D shows application of vacuum into a glass tube using a syringe.

The present invention now will be described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes", "comprises" and/or "comprising," when used in this specification, specify the presence of stated features, integers, steps, operations, elements, and/or components, but do not preclude the presence or addition of one or more other features, integers, steps, operations, elements, components, and/or groups thereof. In addition, a term such as a "unit", a "module", a "block" or like, when used in the specification, represents a unit that processes at least one function or operation, and the unit or the like may be implemented by hardware or software or a combination of hardware and software.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Preferred embodiments will now be described more fully hereinafter with reference to the accompanying drawings. However, they may be embodied in different forms and should not be construed as limited to the embodiments set forth herein. Rather, these embodiments are provided so that this disclosure will be thorough and complete, and will fully convey the scope of the disclosure to those skilled in the art.

Example 1: Porous Nerve Conduit 1-1: Preparation of Porous PLGA Nerve Conduit

A 20% (w/v) PLGA-TG solution (polymer material) was prepared by mixing the hydrophobic polymer poly(lactic acid-co-glycolic acid) (PLGA) (lactic acid/glycolic acid mol %, 85:15) and the water-miscible solvent tetraglycol (TG) (density: 1.09 g/mL, Sigma-Aldrich, USA) at a weight/volume (w/v) ratio of 20% (w/v) and then dissolving at 60° C. for 18 hours.

A glass capillary with an inner diameter of 1.6 mm and a length of 13 cm was heated at the center portion to form a bottleneck, thereby forming upper and lower channels sloped with a discontinuous angle. The lower channels were formed to have smaller diameters than the upper channel. Then, 7000-8500 strands of a water-soluble glass fiber ($50P_2O_5$-$20CaO$-$30Na_2O$ in mol % (1100° C., 800 rpm)) with diameters of 10-20 μm were cut to 5-6 cm and inserted densely into the upper channels of the glass tube along the axis direction (FIG. 1A and FIG. 2A).

A pressure device prepared by connecting a Luer lock syringe equipped with a silicone tube of an inner diameter of 0.8 mm and a length of 15 cm, coupled with a 2-way valve, to the upper channels of the glass fiber-inserted glass tube (FIG. 1B and FIG. 1C).

Figure 2:
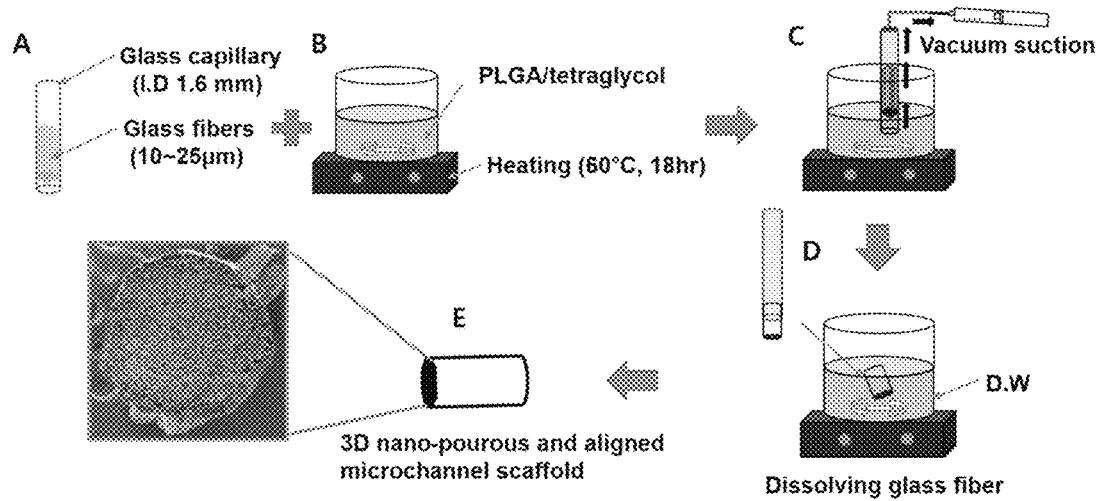
FIG. 2 schematically shows a method for preparing a porous nerve conduit.

After immersing the lower channels of the glass tube in the 20% (w/v) PLGA-TG solution at room temperature, vacuum was repeatedly applied into the glass tube using a syringe such that the 20% (w/v) PLGA-TG solution was completely infiltrated into the void space between the glass fibers (FIG. 1D and FIG. 2C).

Figure 3A:
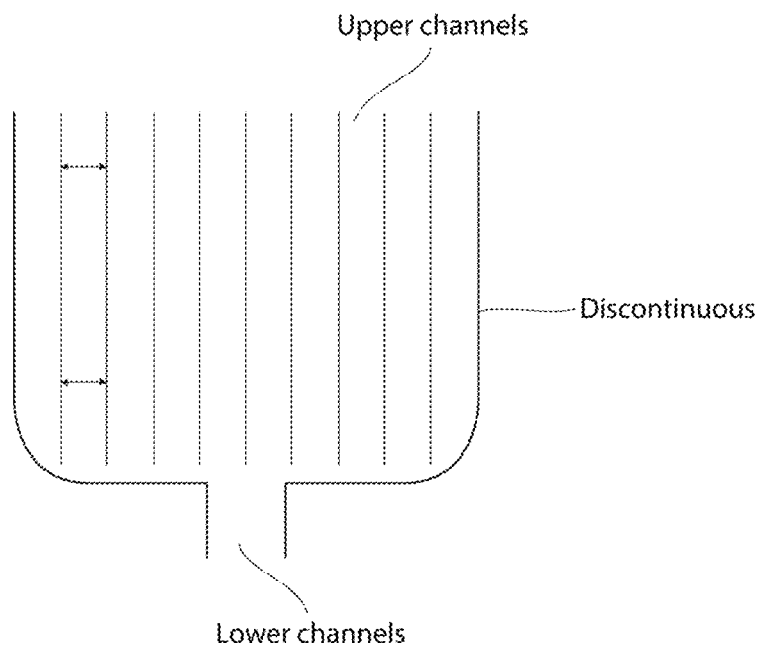
FIG. 3A and FIG. 3B show channel formation in a container with a discontinuous (A) or continuous (B) slope.
Figure 3B:
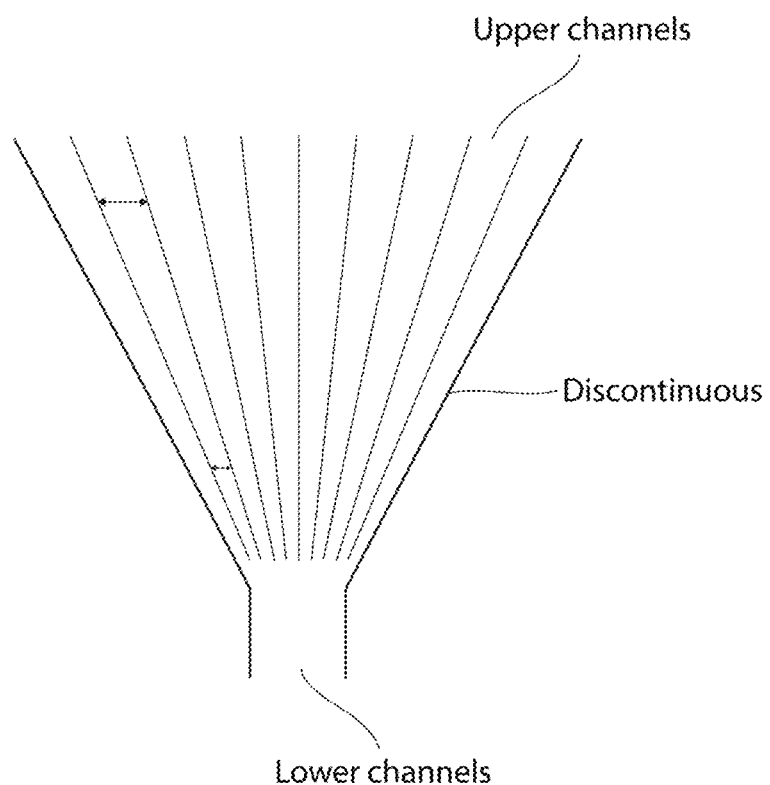

The specific configuration of the glass tube (container) is shown in FIG. 3A. As shown in FIG. 3A, the diameter of the lower channels was decreased than that of the upper channels with a discontinuous angle. If the angle is continuous (FIG. 3B), it is difficult to maintain constant intervals between the glass fibers because the intervals between the glass fibers decrease gradually.

If the nerve conduit is prepared in the state where the intervals between the glass fibers are not constant, the intervals between the microchannels of the nerve conduit will not be constant too. Then, the direction of nerve regeneration induced by the glass fibers will be different depending on the microchannel. As a result, it is difficult to induce nerve regeneration in the same direction.

Figure 4:
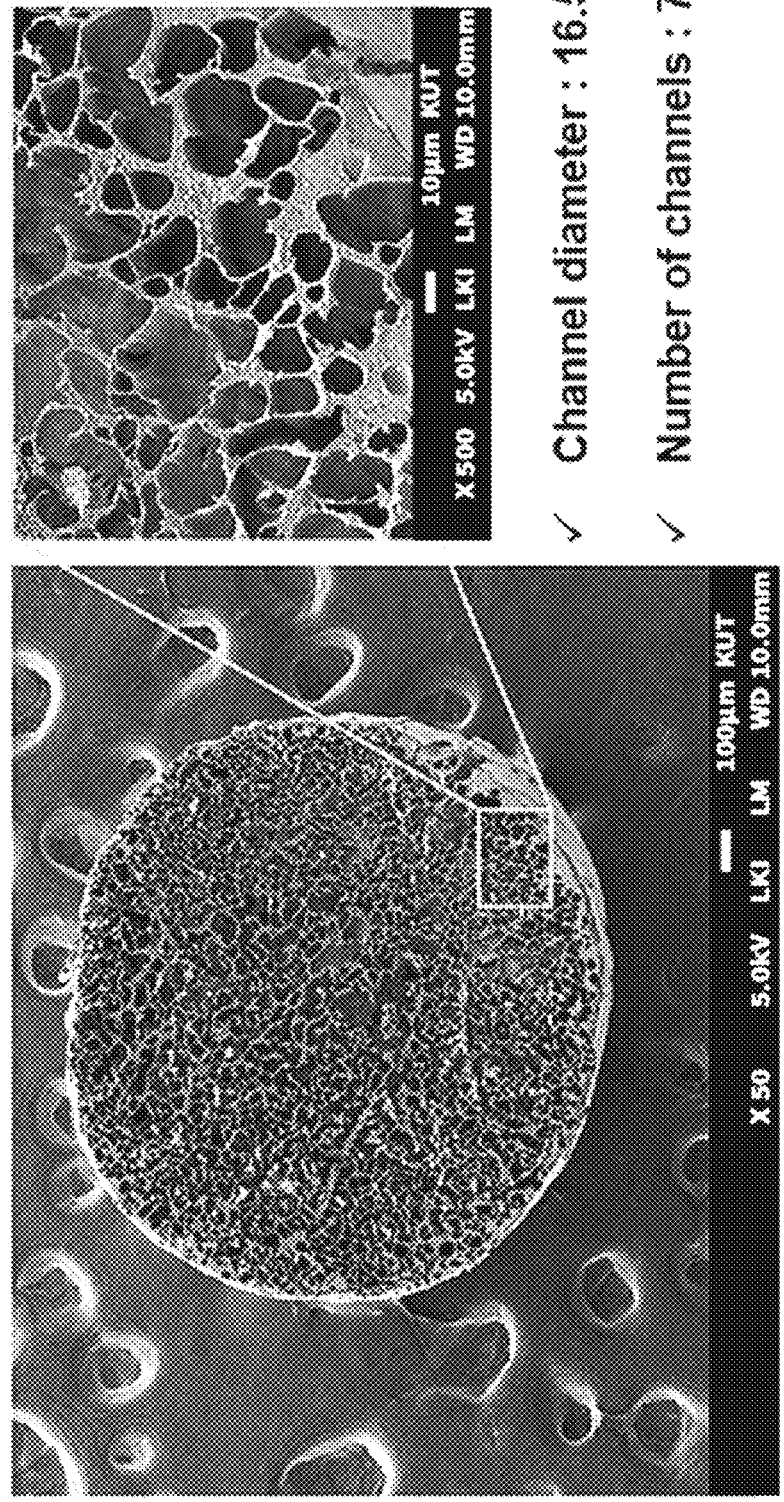
FIG. 4 shows transverse cross-sectional SEM images of a porous PLGA nerve conduit; scale bar=(left) 100 µm, (right) 10 µm.
Figure 5:
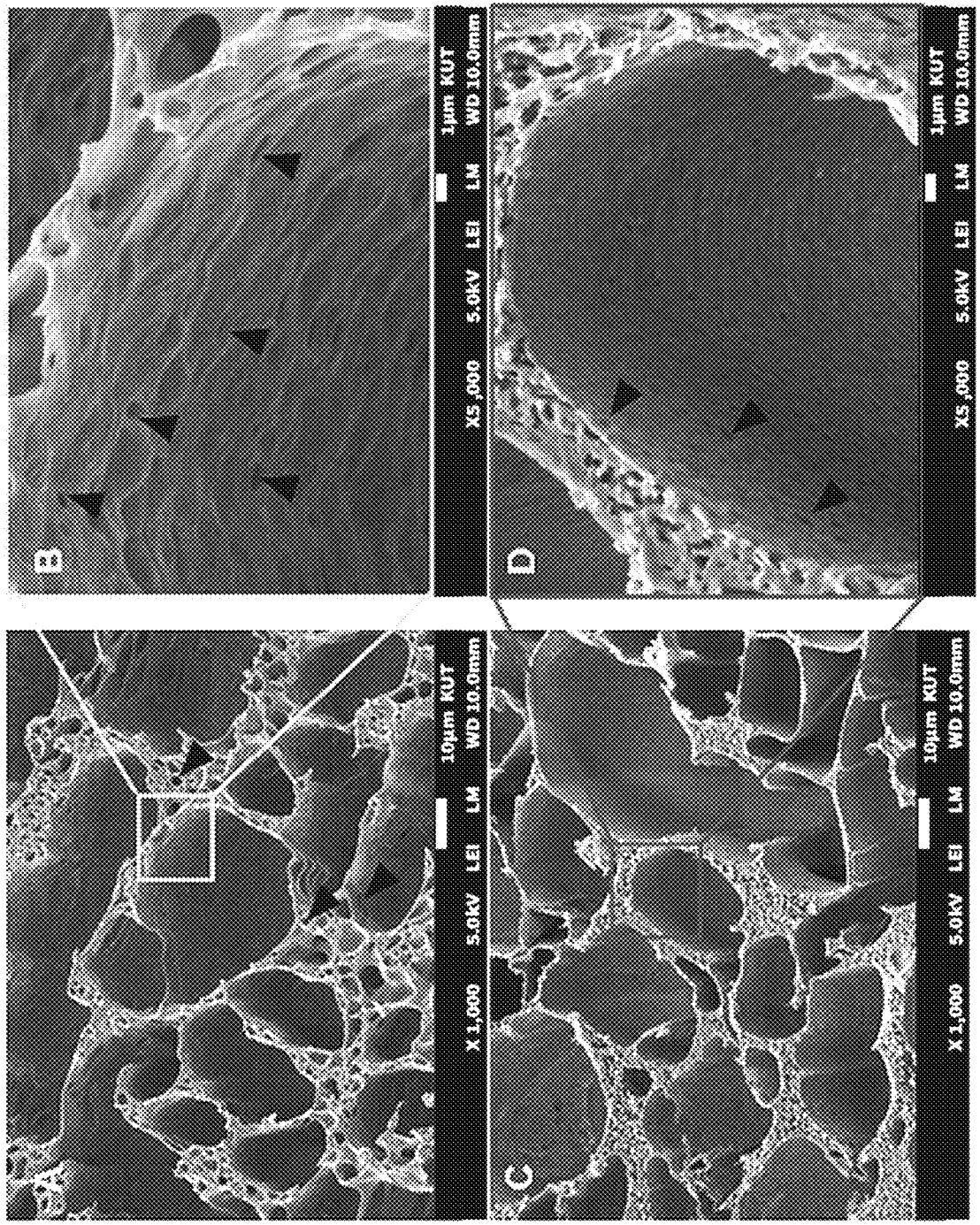
FIG. 5 shows magnified SEM images showing a microstructure at the transverse cross section of a porous nerve conduit; scale bar=(A, C) 10 µm, (B, D) 1 µm, ▶=micropores inside microchannels.
Figure 6:
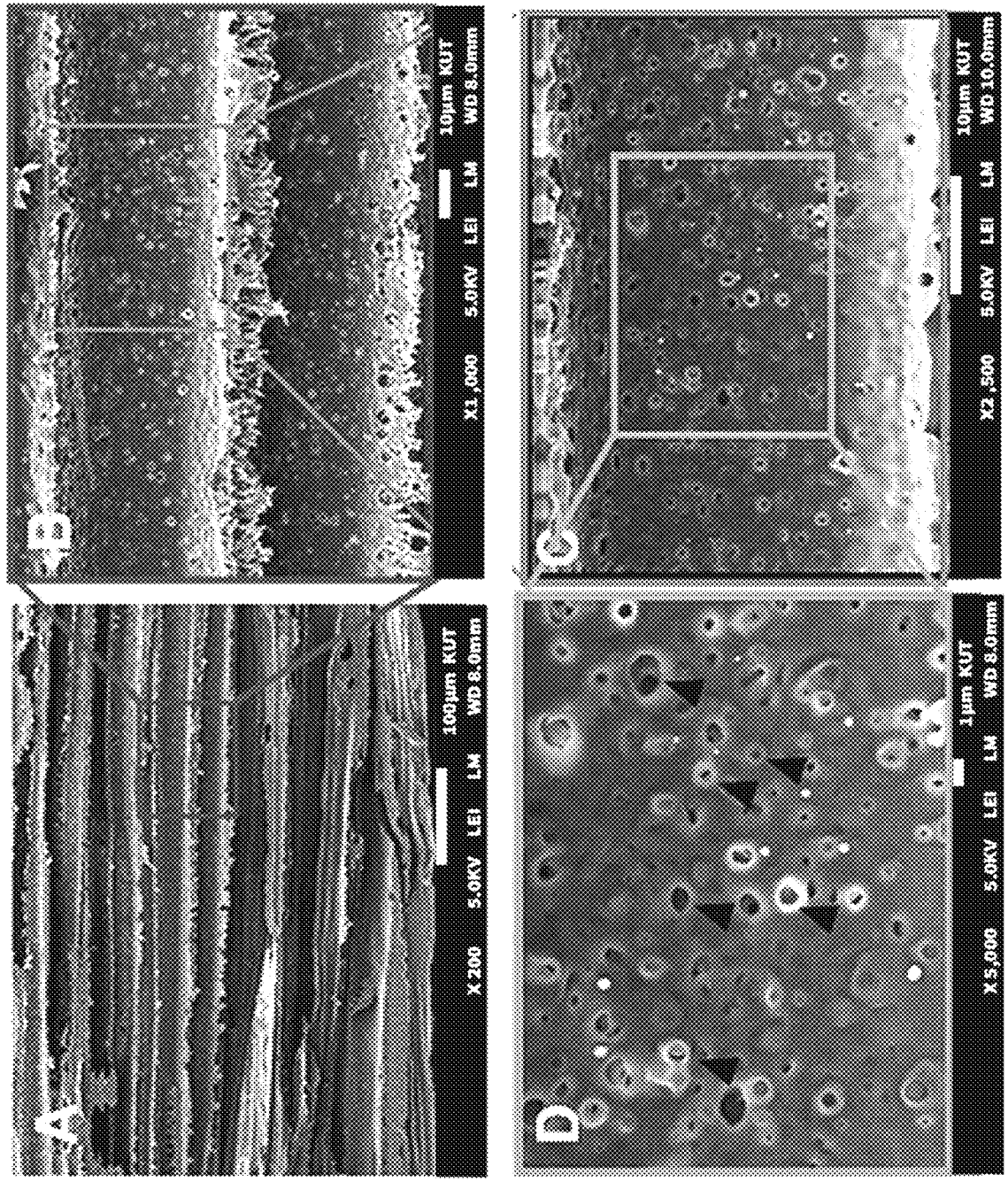
FIG. 6 shows longitudinal cross-sectional SEM images of a porous nerve conduit; scale bar=(A) 100 µm, (B) 10 µm, (C) 10 µm, (D) 1 µm, ▶=micropores inside microchannels.
Figure 7:
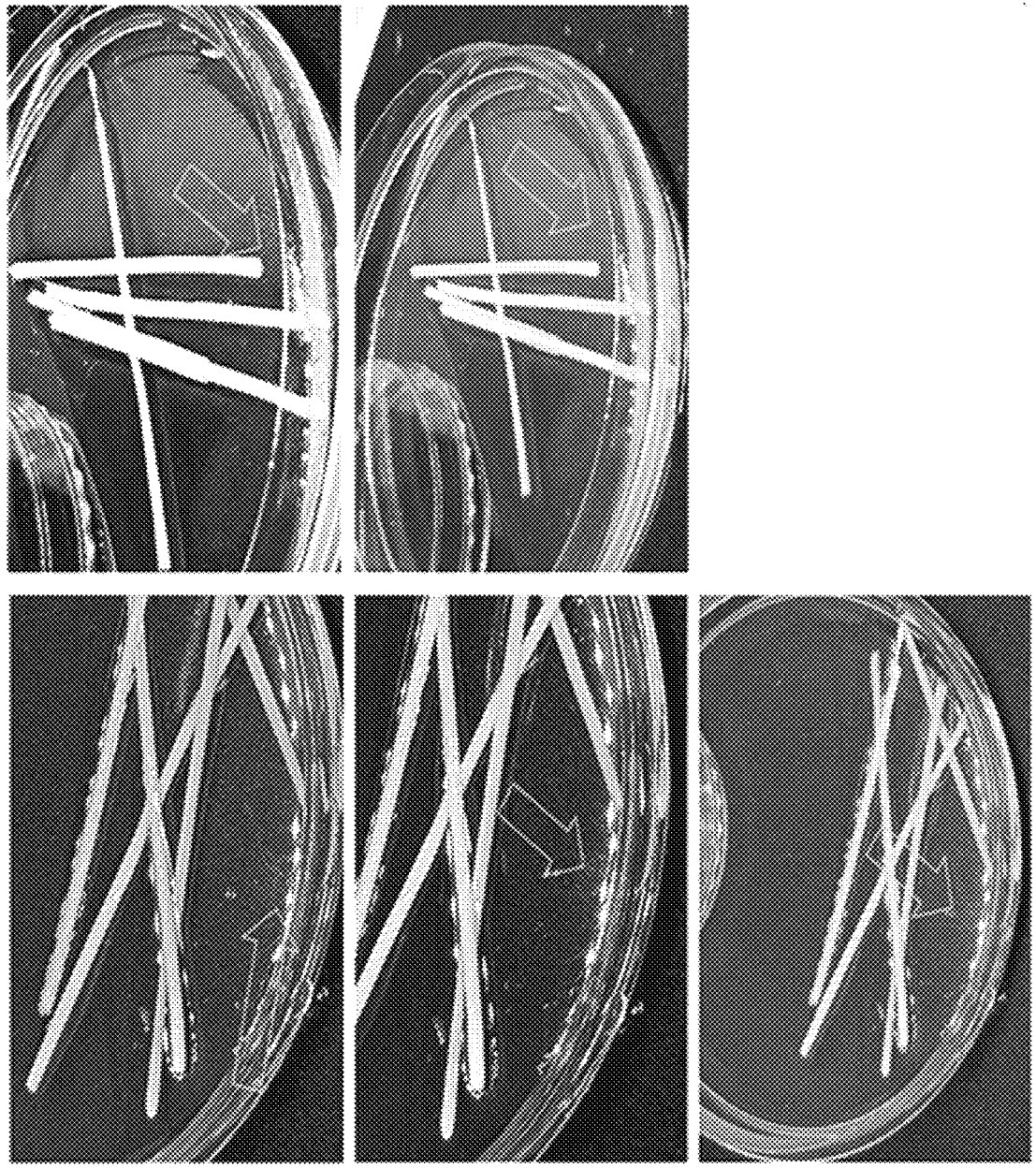
FIG. 7 shows TG released from a porous nerve conduit and submerged in distilled water (DW); arrow: TG.

The PLGA-TG solution-infiltrated glass fibers were separated from the glass tube using a wire with a diameter of 1.5 mm and a length of 15 cm and, immediately thereafter, completely immersed in distilled water (DW) at 10-20° C. for at least 24 hours (FIG. 2D), so that the glass fibers were completely dissolved, and about 7,000-8,500 (7,777±716.2) microchannels of PLGA, with diameters of 10-20 µm (16.54±3.6 µm), were formed in the space where the glass fibers had been dissolved (FIG. 2E and FIG. 4). The microchannels were formed as the glass fibers were dissolved in the water at 10-20° C. and the hydrophobic polymer PLGA was cured at the same time. Also, micropores were formed inside the microchannels as the TG was mixed with the water and released from the hydrophobic polymer while the glass fibers infiltrated with the PLGA-TG solution were immersed in the DW (FIG. 4, FIG. 5 and FIG. 6). Because the TG released from the nerve conduit had a higher density than the DW, it was submerged like heat haze in the DW (FIG. 7).

Figure 8:
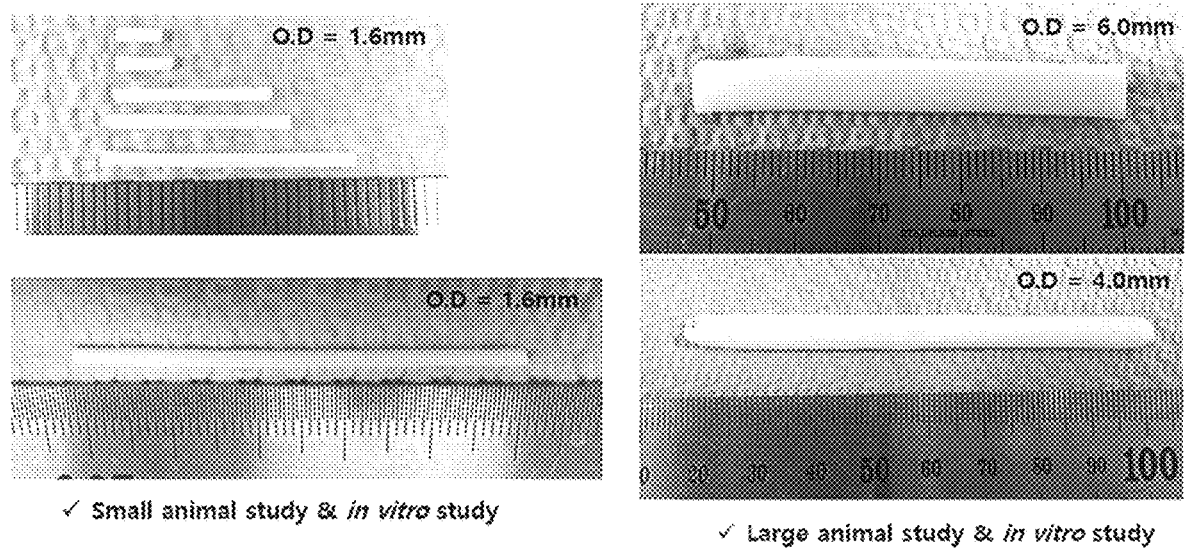
FIG. 8 shows porous nerve conduits prepared with various diameters and lengths depending on applications.

After the glass fibers and the TG were removed through the treatment with DW, the prepared porous microchannels formed of PLGA, i.e., the nerve conduit, was frozen in liquid nitrogen for about 30 seconds, cut to a desired size and then shaped into a desired shape (FIG. 8).

1-2: Investigation of Microstructure Inside Porous PLGA Nerve Conduit

The microstructure formed in the microchannels inside the nerve conduit prepared in Example 1-1 was investigated by scanning electron microscopy (SEM) (FIG. 4, FIG. 5 and FIG. 6).

FIG. 4 shows the transverse cross section of the nerve conduit, FIG. 5 shows magnified images showing the microstructure at the transverse cross section of the nerve conduit and FIG. 6 shows the longitudinal cross section of the nerve conduit. It can be seen that the microchannels were formed continuously inside the nerve conduit and micropores were formed in the microstructure.

1-3: 3D Micro-CT Imaging of Porous Nerve Conduit

Figure 9:
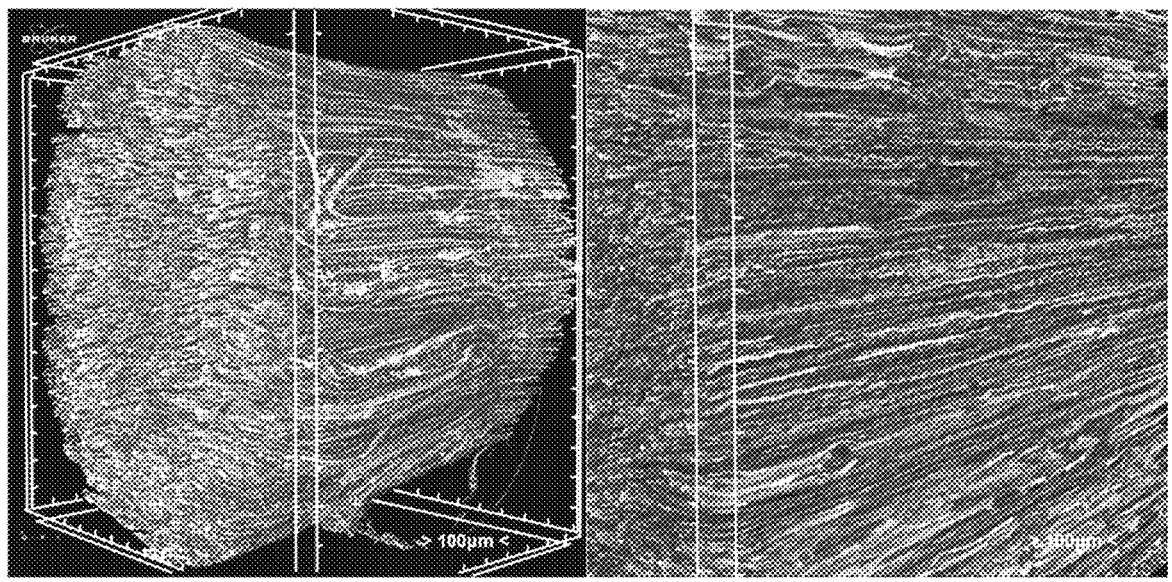
FIG. 9 shows 3D micro-CT images (sagittal plane) of a nerve conduit prepared according to an exemplary embodiment of the present invention.

The 3D CT images of the nerve conduit of Example 1-1 are shown in FIG. 9. Intact microchannels inside the nerve conduit are observed as seen from FIG. 9.

1-4: Preparation of Porous PCL Nerve Conduit

Figure 10:
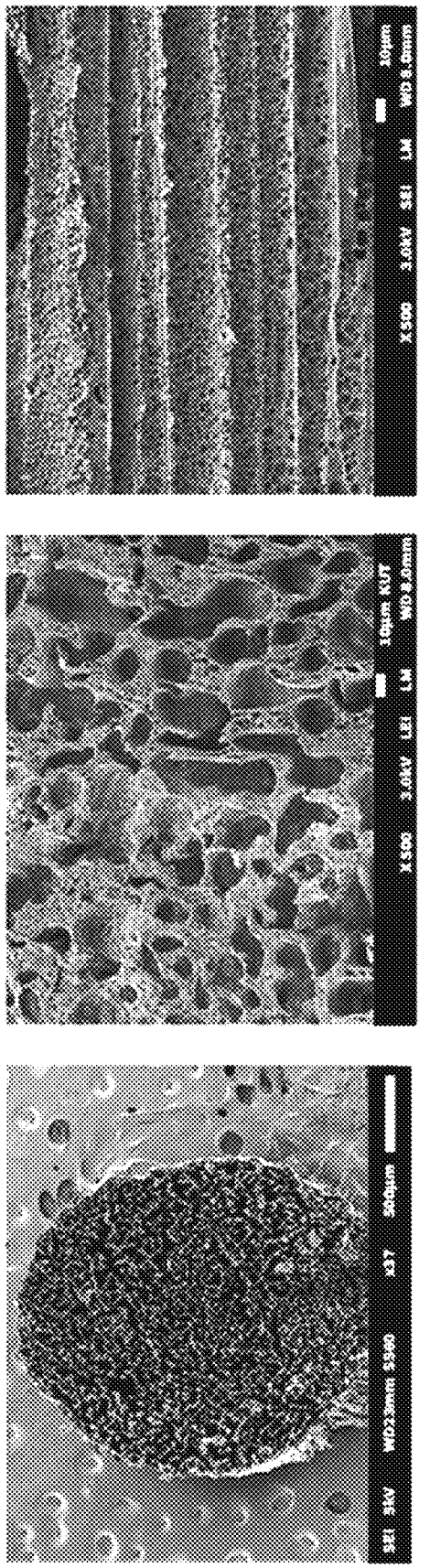
FIG. 10 shows transverse cross-sectional SEM images of a porous PCL nerve conduit; scale bar=(left) 500 μm, (center) 10 μm (right) 10 μm. A shows a transverse cross-sectional image, B shows a magnified transverse cross-sectional SEM images showing a microstructure, and C shows a longitudinal cross-sectional image.

A porous nerve conduit was prepared in the same manner as in Example 1-1 except that the polymer material was prepared using polycaprolactone (PCL) as the hydrophobic biocompatible polymer material instead of the PLGA. As the polymer material, an 18% (w/v) PCL-TG solution was prepared by mixing PCL and TG at a weight/volume (w/v) ratio of 18% (w/v) and then dissolving at 90° C. for 18-24 hours. Then, a nerve conduit was prepared in the same manner as in Example 1-1 (FIG. 10).

Example 2: Porous Nerve Conduit Containing Cells 2-1: Preparation of Cell Seeding System First, a chamber formed of polydimethylsiloxane (PDMS) with dimensions shown in FIG. 11A and FIG. 11B was prepared. A method for preparing the PDMS chamber is well known in the art. Specifically, it was prepared by fabricating a mold of a desired shape using, e.g., a 3D printer, pouring a PDMS solution into the mold and then curing the same by heating.

Figure 11:
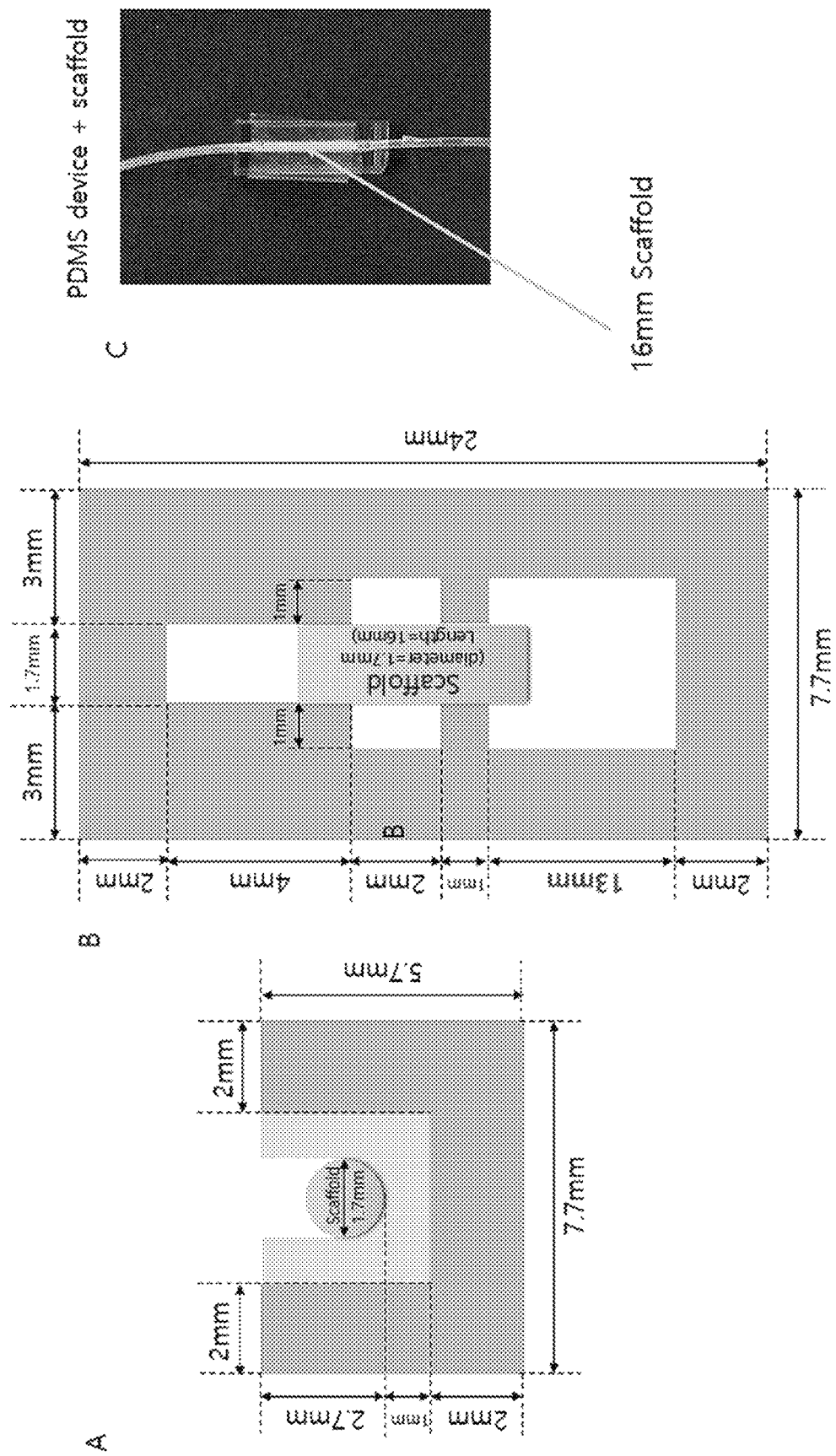
FIG. 11 shows the dimension of a PDMS chamber (A, B) and a PDMS device sealed by covering with a cover glass (C).
Figure 12:
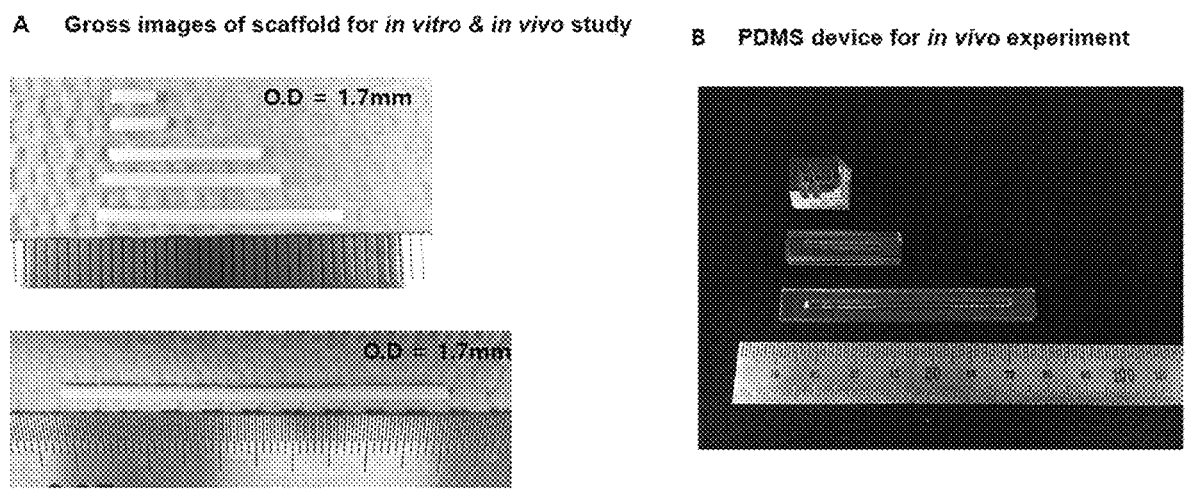
FIG. 12 shows nerve conduits of various lengths and PDMS chambers of various lengths prepared therefrom.

After inserting the nerve conduit of Example 1 with a diameter of 1.6-1.7 mm and a length 16 mm in the PDMS chamber, 4% agarose completely dissolved in water was cooled to 40-50° C. and then filled into the space between the PDMS chamber and the nerve conduit. After keeping at room temperature for 5 minutes, so that the agarose was completely cured, and making the agarose and PDMS chamber surface even, a PDMS device was prepared by sealing by covering with a cover glass (FIG. 11C). Care was taken to prevent the agarose from infiltrating the upper and lower end portions of the nerve conduit and blocking microchannels. Because the nerve conduit can be prepared to have various lengths, PDMS devices of various lengths can be prepared accordingly (FIG. 12).

Figure 13:
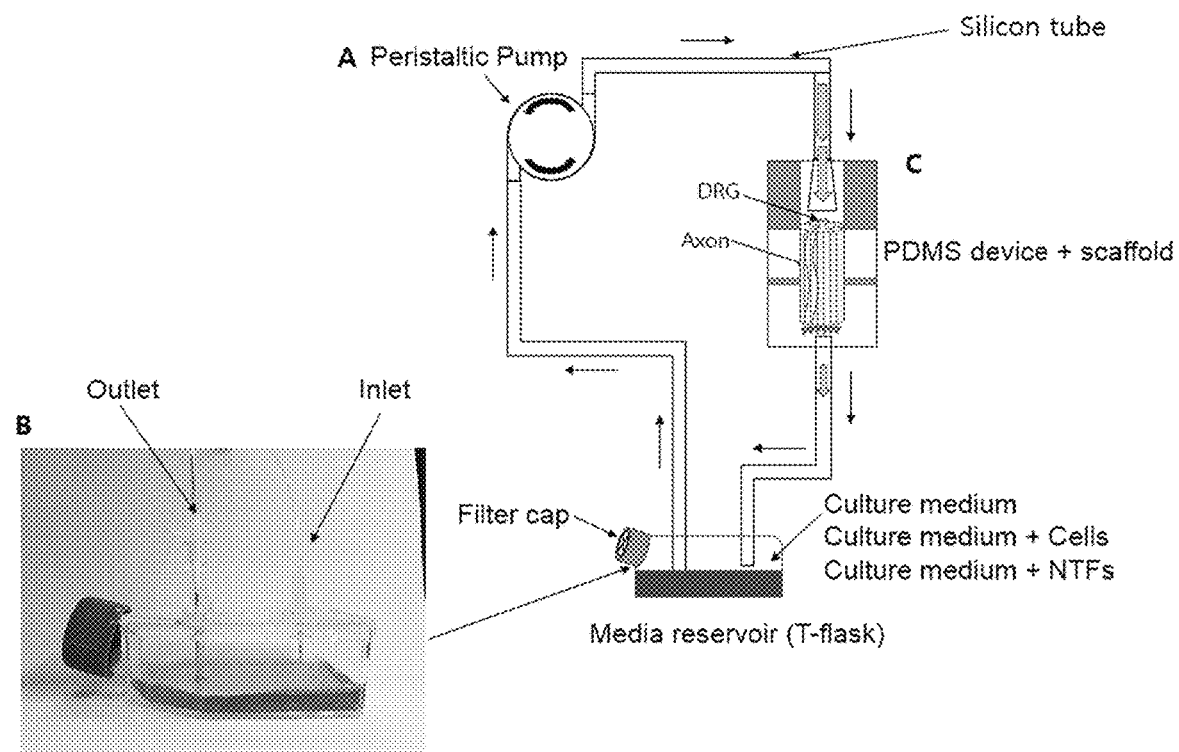
FIG. 13 shows a schematic of an in-vitro nerve cell culturing device (A) and a photographic image of a medium reservoir (B).
Figure 14:
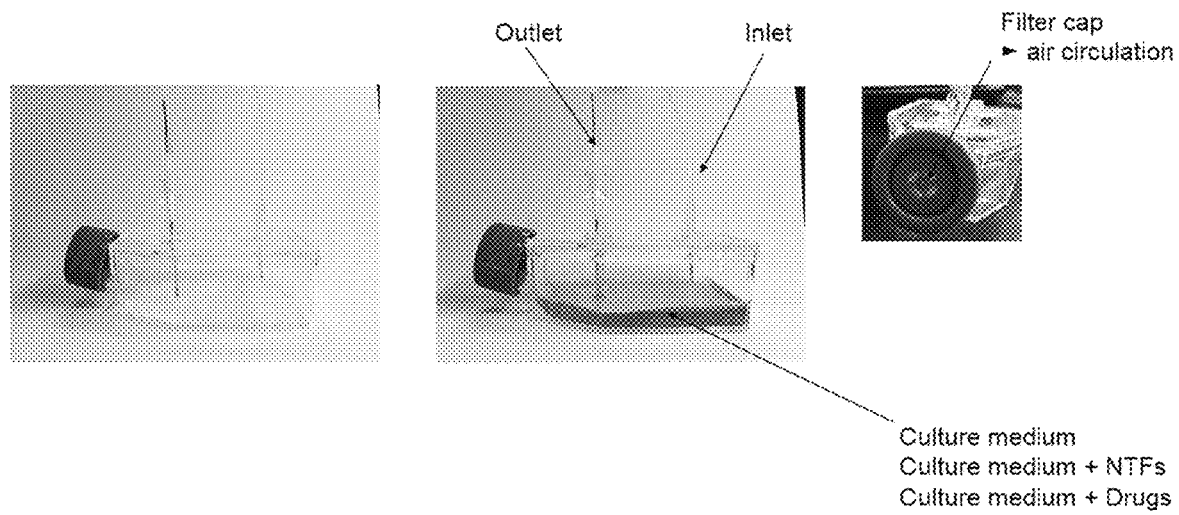
FIG. 14 shows the configuration of a medium reservoir.

Then, a cell seeding system was prepared by connecting a multichannel peristaltic pump (Gilson's Minipuls 3) to the upper portion of the nerve conduit-inserted PDMS device using a silicone tube (FIG. 13A) and connecting a medium reservoir prepared by modifying a 25-mL T-flask to the lower portion (FIG. 13B and FIG. 14). The top portion of the 25-mL T-flask was perforated and a needle and a tube for injection (inlet) and discharge (outlet) were inserted. The T-flask was equipped with a filter cap to prevent contamination while allowing air flow. The prepared cell seeding system supplied a culture medium from the medium reservoir to the nerve conduit-inserted PDMS device using the pump.

2-2: Seeding of Schwann Cells

Schwann cells were isolated from the sciatic nerve of a wild-type or green fluorescent protein (GFP)-expressing 6-week-old SD (Sprague Dawley) rat (SD-Tg(CAG-EGFP) rat) (Japan SLC, Hamamatsu-shi, Shizuoka, Japan).

Figure 15:
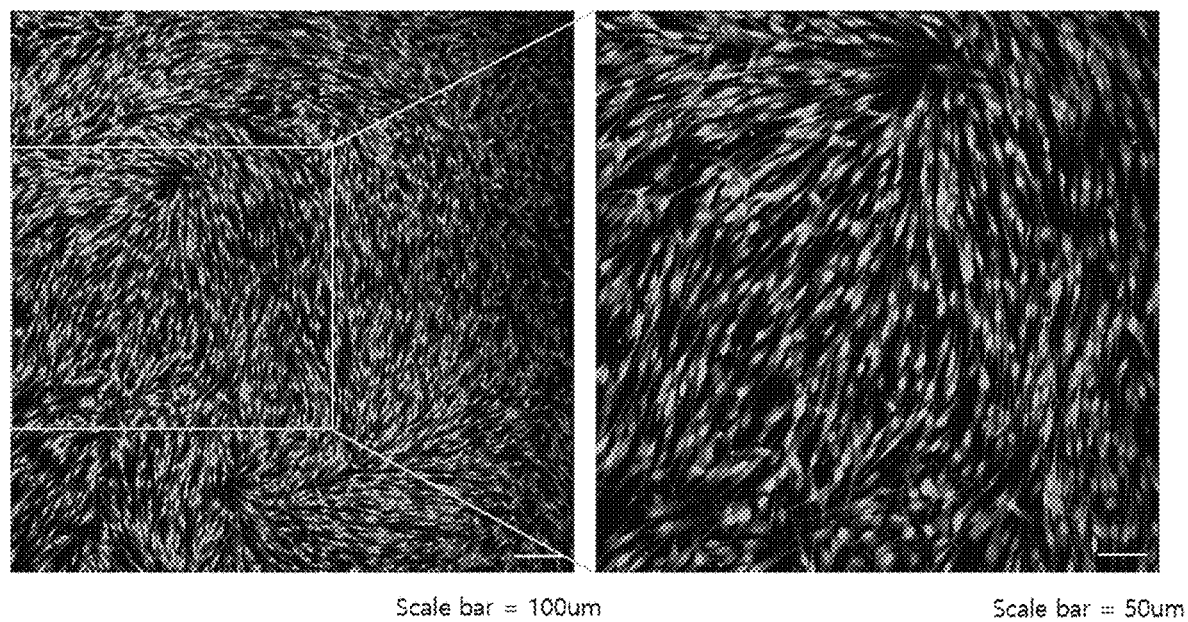
FIG. 15 shows primarily cultured sciatic nerve-derived Schwann cells of a rat.
Figure 16:
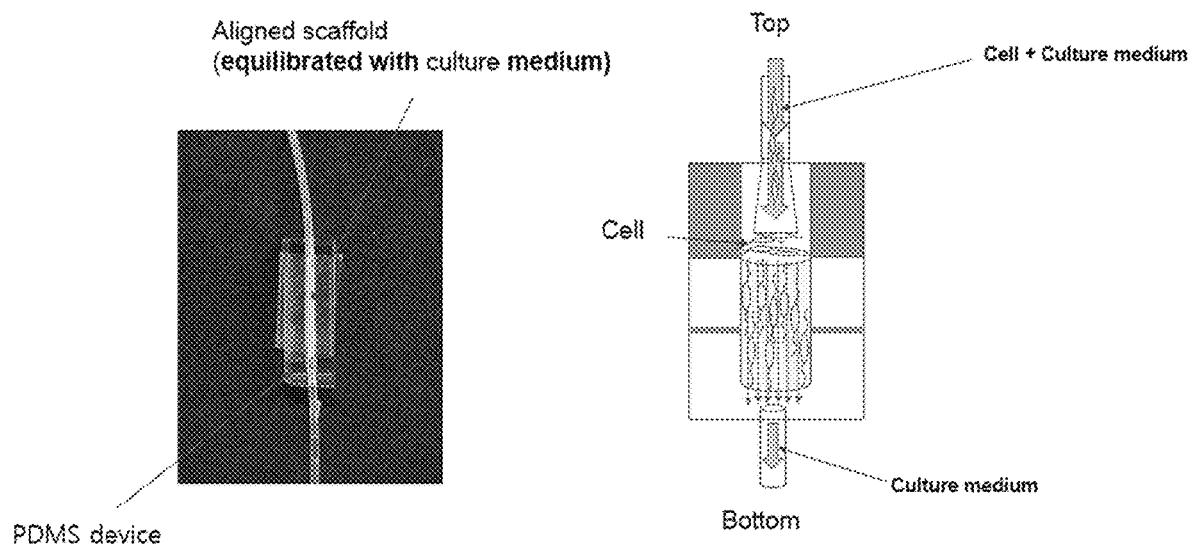
FIG. 16 shows a photographic image and a schematic of a Schwann cell seeding procedure using a pump.

In order to seed the Schwann cells into the nerve conduit, the primarily cultured 2×10$^5$ Schwann cells were diluted in 5-10 mL of a culture medium (FIG. 15) and then put in the medium reservoir. The Schwann cells were seeded into the nerve conduit at a speed of 50 µL/min using the peristaltic pump (FIG. 16). The diameter of the microchannels inside the nerve conduit was 10-20 µm and the culture medium containing the Schwann cells with a diameter of about 15 µm was flown continuously so that the Schwann cells could infiltrate the microchannels inside the nerve conduit.

2-3: Culturing of Schwann Cells

Figure 17:
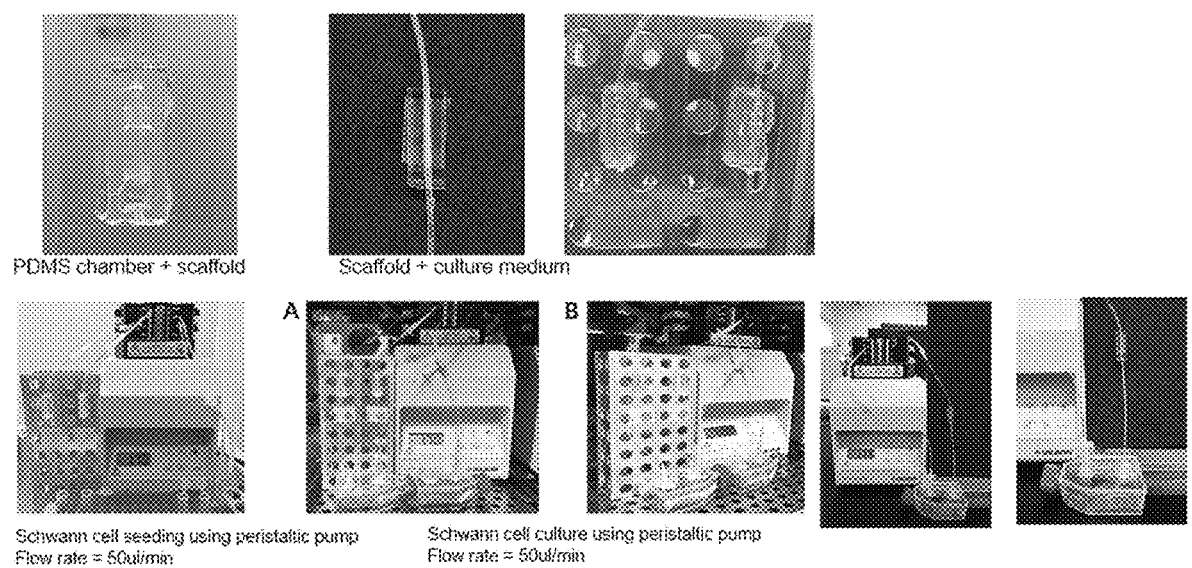
FIG. 17 shows an example of using a device for seeding Schwann cells into a nerve conduit.
Figure 18:
FIG. 18 shows an example of using a device for seeding Schwann cells into a nerve conduit.

After the seeding of the Schwann cells, a culture medium containing a nerve-related growth factor or a drug was put in the medium reservoir and the peristaltic pump was operated such that the culture medium was flown from the upper portion of the nerve conduit to the lower portion. The flow rate of the culture medium was maintained at 50 μL/min or lower and the Schwann cells were cultured for 1-3 days in a $CO_2$ incubator while continuously flowing the culture medium (FIG. 17 and FIG. 18). During the culturing, the nerve conduit was erected vertically to prevent the unattached Schwann cells from falling to the space other than the nerve conduit.

2-4: Confirmation of Seeded Schwann Cells

Figure 19:
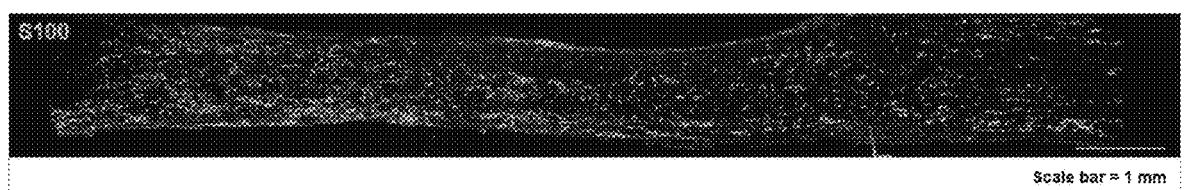
FIG. 19 shows a result of culturing Schwann cells expressing the fluorescent protein EGFP in a nerve conduit with a diameter of 1.6-1.7 mm and a length 16 of mm for 3 days and then imaging the cells by confocal microscopy.

As a result of seeding the Schwann cells into the microchannels inside the nerve conduit and culturing for 3 days, it was confirmed by confocal microscopy that the Schwann cells were growing along the microchannels (FIG. 19).

Figure 20:
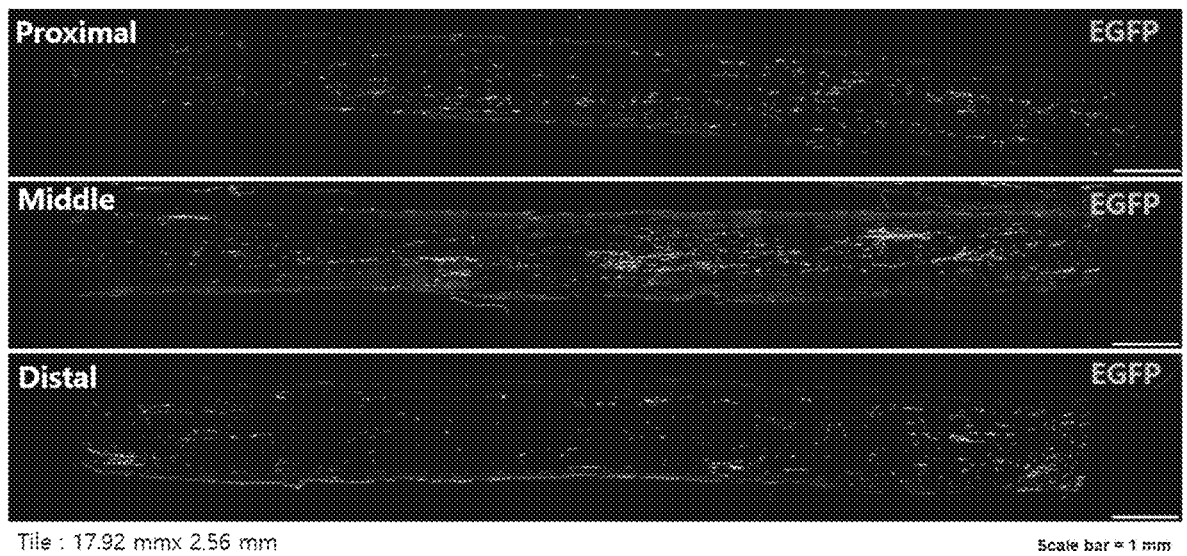
FIG. 20 shows a result of culturing Schwann cells expressing the fluorescent protein EGFP in a nerve conduit with a diameter of 1.7 mm and a length 50 of mm for 3 days and then imaging the cells by confocal microscopy.
Figure 21:
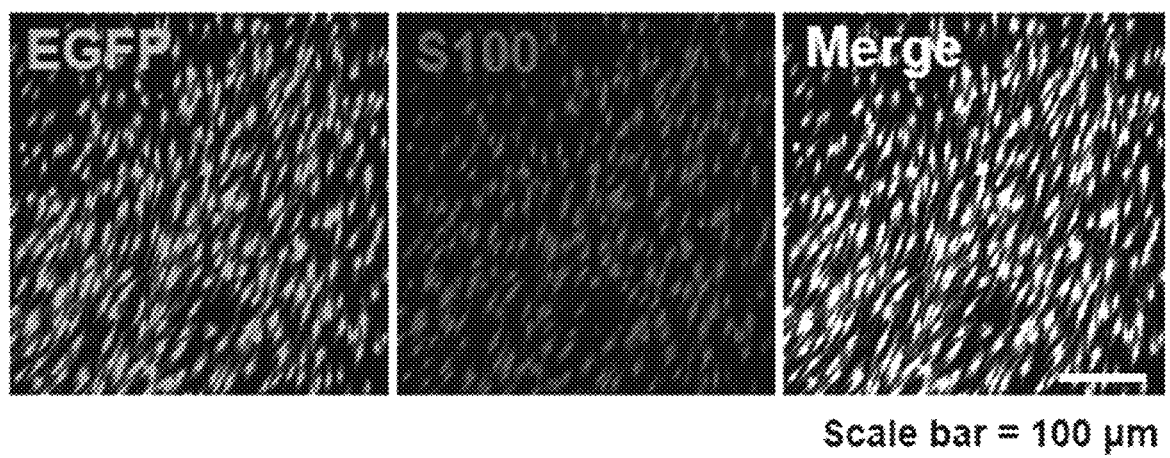
FIG. 21 shows the images of EGFP-labeled Schwann cells (EGFP) and Schwann cells stained with rabbit S100 polyclonal antibody (S100) as well as a merged image of the EGFP-labeled Schwann cells and the Schwann cells stained with rabbit S100 polyclonal antibody (Merge).

Also, as a result of seeding $4 \times 10^5$ Schwann cells into a nerve conduit with a diameter of 1.7 mm and a length of 50 mm, which was prepared by the method of Example 1 for nerve transplantation of large animals, and culturing for 3 days, it was confirmed by confocal microscopy that the Schwann cells were growing throughout the full length of 50 mm (FIG. 20).

2-5: Confirmation of Schwann Cells Seeded by Direct Injection or Cell Seeding System After seeding Schwann cells into a nerve conduit by direct injection or a cell seeding system, the growth pattern of the Schwann cells was compared. Specifically, Schwann cells prepared with a concentration of $5 \times 10^5$ cells/10 μL were directly injected into a porous PLGA nerve conduit (length=16 mm, O.D.=2.2 mm) using a Hamilton syringe or seeded by a cell seeding system with a culture medium flow rate of 20 μL/min and then cultured for 3 days, respectively.

Figure 22:
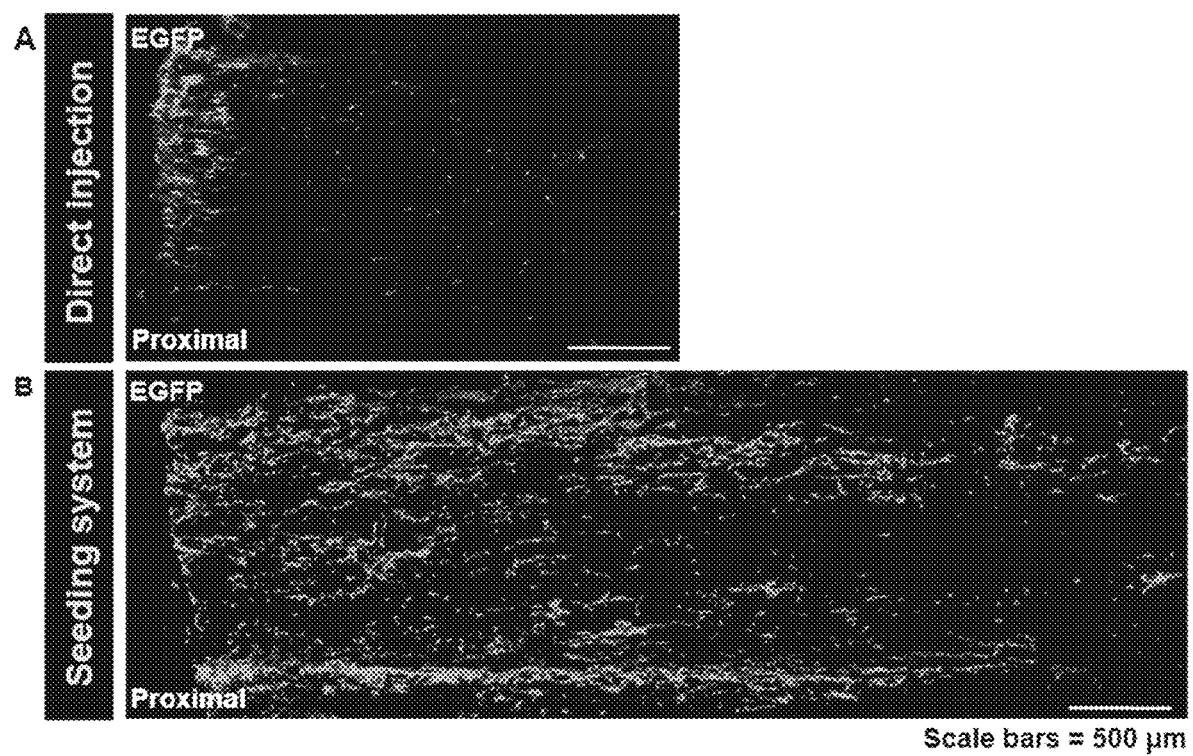
FIG. 22 shows Schwann cells imaged by confocal microscopy, which were cultured for 3 days after seeding by direct injection (A) or using a cell seeding system (B).

When observed by confocal microscopy, the Schwann cells seeded using the cell seeding system were growing throughout the full length of the nerve conduit (FIG. 22B), whereas the Schwann cells seeded by direct injection were growing only at the injected area (FIG. 22A).

Example 3: Confirmation of Nerve Regeneration Effect In Vitro

DRG explants were obtained by isolating DRGs (dorsal root ganglia) from the thoracic and lumbar area of a 3-day-old SD rat and culturing the same.

Schwann cells and the DRG explants were seeded into a porous PCL nerve conduit (length=16 mm, O.D.=2.2 mm) using the cell seeding system of Example 2 and then cultured. Specifically, $5 \times 10^5$ cells/scaffold of Schwann cells were seeded with a culture medium flow rate of 20 μL/min and then cultured for 1 day. And, 3-5 DRG explants/scaffold were seeded with a culture medium flow rate of 20 μL/min and then cultured for 1 day.

The result of seeding 3-5 DRG explants into the nerve conduit and culturing for 1 day or seeding Schwann cells into the nerve conduit, culturing for 1 day, seeding 3-5 DRG explants and then culturing for 1 day was compared by immunostaining. Mouse Tuj1 monoclonal antibody was used for staining of the axons of the nerve cells and rabbit S100 polyclonal antibody was used for staining of the Schwann cells.

Figure 23:
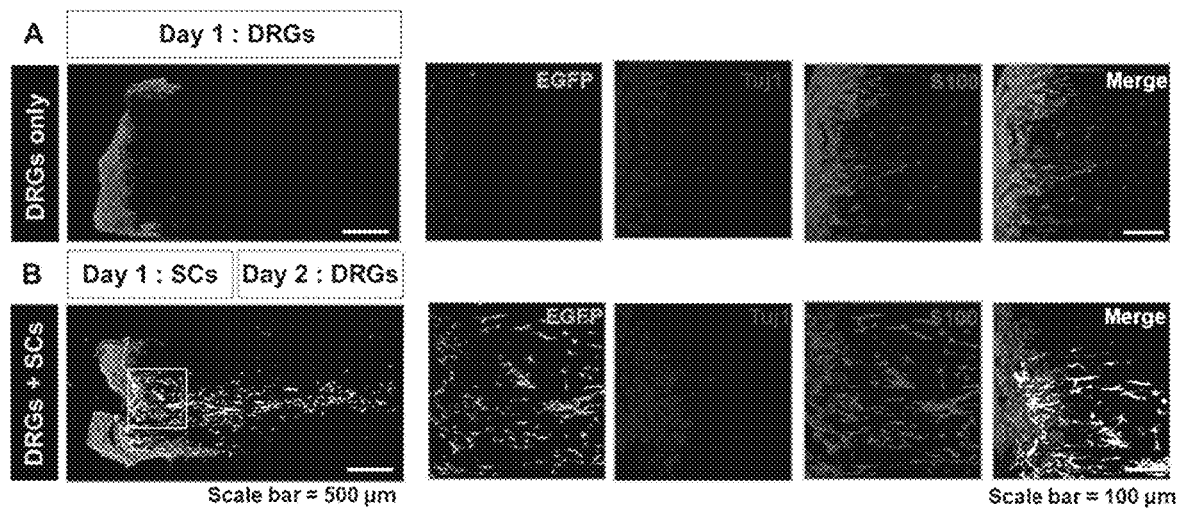
FIG. 23 shows a result of seeding 3-5 DRG explants into a nerve conduit and culturing for 1 day (A) or seeding Schwann cells into a nerve conduit, culturing for 1 day, seeding 3-5 DRG explants and then culturing for 1 day (B), imaged by confocal microscopy.

When observed by confocal microscopy, axons (Tuj1) and Schwann cells (S100) were observed at the distal part when the Schwann cells were seeded and then the DRG explants were seeded (FIG. 23B) as compared to when only the DRG explants were seeded (FIG. 23A). EGFP indicates the Schwann cells primarily cultured from the SD-Tg (CAG-EGFP) rat.

This result proves that the nerve conduit containing Schwann cells is effective for nerve regeneration.

Example 4: Confirmation of Nerve Regeneration Effect In Vivo

Figure 24:
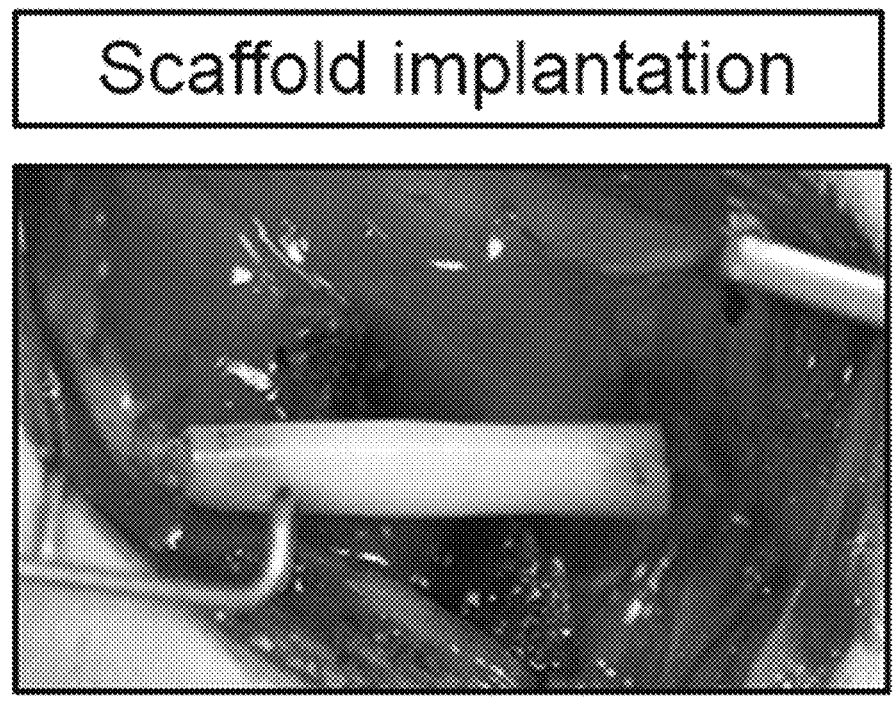
FIG. 24 illustrates an in-vivo experiment procedure for confirming the nerve regeneration effect of a nerve conduit according to the present invention, showing an image of a 16-mm nerve conduit inserted after cutting the sciatic nerve of a rat.

After removing the sciatic nerve (length 16 mm) of a 12-week-old SD rat (female, 230-250 g), $5 \times 10^5$ cells/scaffold of Schwann cells seeded into a PCL nerve conduit (length=16 mm, O.D.=2.2 mm) and cultured for 1 day were transplanted into the damaged area as shown in FIG. 24. As a control group, a PCL nerve conduit without seeding Schwann cells was transplanted. In order to prevent the nerve conduit from being separated from the nerve, the both ends of the nerve conduit were sutured to the cut nerve terminals using a suture (10-0: 0.02-0.029 mm thick nylon suture).

Figure 25:
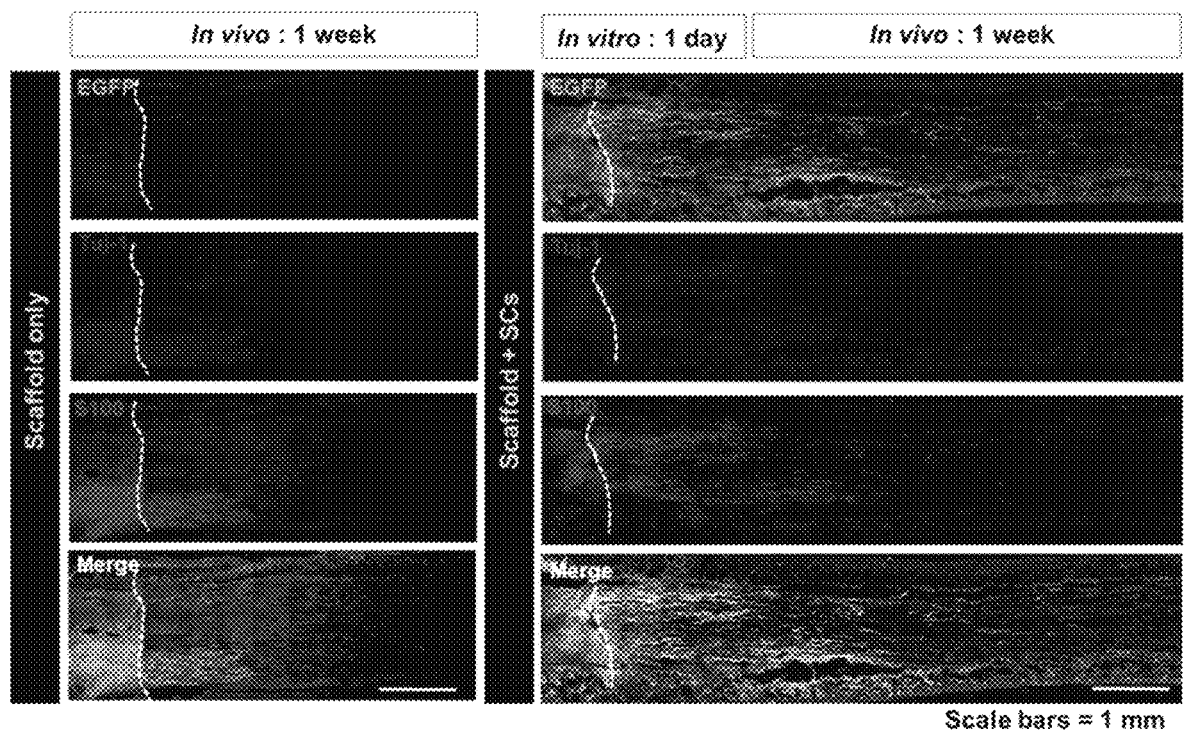
FIG. 25 shows a result of an in-vivo experiment for confirming the nerve regeneration effect of a nerve conduit according to the present invention. One week after implantation of the nerve conduit, axons (stained with Tuj1 monoclonal antibody) and Schwann cells (stained with S100 polyclonal antibody) were observed at the distal part in the animal into which a Schwann cell-seeded nerve conduit was transplanted (Scaffold+SCs) as compared to the animal into which only the nerve conduit was transplanted (Scaffold only). EGFP indicates Schwann cells primarily cultured from a SD-Tg (CAG-EGFP) rat. Merge indicates a merged image of EGFP-labeled fluorescent Schwann cells, axons stained with Tuj1 monoclonal antibody and Schwann cells stained with S100 polyclonal antibody.

One week after the transplantation, immunostaining was conducted to check the growth of the sciatic nerve. The sciatic nerve containing the 18-mm long graft was taken out and fixed in 4% paraformaldehyde. Then, after treating with 30% sucrose for 3 days, the tissue was sliced to 16-μm thick sections. Mouse Tuj1 monoclonal antibody was used for staining of the neuronal axons and rabbit S100 polyclonal antibody was used for staining of the Schwann cells. The tissue sections were observed with a confocal microscope and the result is shown in FIG. 25. Axons (stained with Tuj1 monoclonal antibody) and Schwann cells (stained with S100 polyclonal antibody) were observed at the distal part in the animal into which a Schwann cell-seeded nerve conduit was transplanted (Scaffold+SCs) as compared to the animal into which only the nerve conduit was transplanted (Scaffold only). The axons appear blue. The seeded Schwann cells appear yellow because they express EGFP and at the same time are stained by S100 (green+red). The Schwann cells derived from the experimental animal, i.e., the existing Schwann cells appear red because they were stained with S100 only. EGFP, which indicates the Schwann cells primarily cultured from the SD-Tg (CAG-EGFP) rat, appear green. Merge indicates a merged image of the EGFP-labeled fluorescent Schwann cells, the axons stained with Tuj1 monoclonal antibody and the Schwann cells stained with S100 polyclonal antibody.

The existing Schwann cells derived from the experimental animal appear pink when the axons are myelinated. However, in FIG. 25, the merged image of the animal into which the Schwann cell-seeded nerve conduit was transplanted exhibits a white portion due to overlapping of green (EGFP: EGFP-labeled Schwann cells), blue (Tuj1: axons) and red (S100: seeded Schwann cells+existing Schwann cells) colors. The white portion indicates that the axons of the experimental animal were myelinated by the seeded Schwann cells.

That is to say, this result proves that the nerve conduit containing Schwann cells is effective for nerve regeneration.

While the present disclosure has been described with reference to the embodiments illustrated in the figures, the embodiments are merely examples, and it will be understood by those skilled in the art that various changes in form and other embodiments equivalent thereto can be performed. Therefore, the technical scope of the disclosure is defined by the technical idea of the appended claims.

The drawings and the forgoing description gave examples of the present invention. The scope of the present invention, however, is by no means limited by these specific examples. Numerous variations, whether explicitly given in the specification or not, such as differences in structure, dimension, and use of material, are possible. The scope of the invention is at least as broad as given by the following claims.

What is claimed is:

1. A method for preparing a porous nerve conduit containing cells comprising:
   a) a step of preparing a polymer material for the nerve conduit by dissolving a hydrophobic biocompatible polymer in a water-miscible organic solvent;
   b) a step of preparing the nerve conduit formed of a porous polymer having micropores formed in microchannels by immersing the polymer material for the nerve conduit in a hydrophilic solution and thereby separating the organic solvent from the polymer material;
   c) a step of preparing a nerve conduit-inserted device by inserting the nerve conduit in a chamber;
   d) a step of connecting a pump to an upper portion of the nerve conduit-inserted device via a tube and connecting a medium reservoir comprising a culture medium to a lower portion of the nerve conduit-inserted device via the tube;
   e) a step of adding cells to the culture medium in the medium reservoir;
   f) a step of seeding the cells into the nerve conduit of the step c) by supplying the culture medium in the medium reservoir of the step e) to the nerve conduit-inserted device using the pump of the step d); and
   g) a step of culturing the cells by supplying the culture medium in the medium reservoir of the step e) to the cell-seeded nerve conduit of the step f) using the pump of the step d),
   wherein the nerve conduit having microchannels is disposed vertically such that the culture medium flows from an upper end of the nerve conduit to a lower end of the nerve conduit by gravity.

2. The method for preparing a porous nerve conduit containing cells of claim 1, wherein the porous nerve conduit is for regeneration of a central nerve or a peripheral nerve.

3. The method for preparing a porous nerve conduit containing cells of claim 1, wherein the hydrophobic biocompatible polymer of the step a) is selected from a group comprising of polylactic acid (PLA), poly-L/D-lactide (PLDA), poly-L-lactic acid (PLLA), polyglycolic acid (PGA), polydioxanone, polyhydroxybutyrate (PHB), polyhydroxyalkanoate (PHA) poly(lactic-co-glycolic acid) (PLGA), polycaprolactone (PCL), a copolymer thereof and a mixture thereof and the water-miscible organic solvent of the step a) is selected from a group comprising of ethanol, isopropyl alcohol, N-methyl-2-pyrrolidone, 2-pyrrolidone, glycerol, propylene glycol, polyethylene glycol, tetraglycol, glycerol formal, ethyl acetate, ethyl lactate, diethyl carbonate, propylene carbonate, acetone, methyl ethyl ketone, dimethyl sulfoxide, dimethyl sulfone, tetrahydrofuran, tetrahydrofurfuryl alcohol, succinic acid diethyl ester, triethyl citrate, dibutyl sebacate, dimethylacetamide, lactic acid butyl ester, propylene glycol diacetate, diethylene glycol monoethyl ether and a mixture thereof.

4. The method for preparing a porous nerve conduit containing cells of claim 1, wherein the polymer material for a nerve conduit of the step a) is one in which the hydrophobic biocompatible polymer is dissolved in the water-miscible organic solvent at a concentration of 10-40 weight/volume % (w/v %).

5. The method for preparing a porous nerve conduit containing cells of claim 1, wherein the nerve conduit formed of a porous polymer having micropores formed in microchannels of the step b) is prepared by:
   a step of inserting a plurality of glass fibers into a container having upper and lower channels;
   a step of injecting the polymer material for the nerve conduit comprising the hydrophobic biocompatible polymer and the water-miscible organic solvent into the container in which the plurality of glass fibers are inserted;
   a step of infiltrating the polymer material between the glass fibers by applying vacuum to the upper channel;
   a step of separating the glass fibers with the polymer material, which was infiltrated from the container; and
   a step of dissolving the glass fibers by immersing the separated glass fibers in the hydrophilic solution,
   wherein the polymer material for a nerve conduit is one in which the hydrophobic biocompatible polymer is dissolved in the water-miscible organic solvent at a concentration of 10-40 weight/volume % (w/v %),
   wherein in the step of dissolving the glass fibers, the microchannels are formed as the hydrophobic biocompatible polymer is cured and the micropores are formed in the microchannels formed of the hydrophobic polymer as the water-miscible organic solvent is mixed with the hydrophilic solution and released from the hydrophobic polymer.

6. The method for preparing a porous nerve conduit containing cells of claim 5, wherein the lower channel has a smaller diameter than the upper channel and the container is sloped with a discontinuous angle.

7. The method for preparing a porous nerve conduit containing cells of claim 5, wherein the polymer material for a nerve conduit is in a solution state at room temperature.

8. The method for preparing a porous nerve conduit containing cells of claim 5, wherein the method for preparing a porous nerve conduit containing cells further comprises, after the step of dissolving the glass fibers:
   a step of cooling the nerve conduit formed after the glass fibers are dissolved; and
   a step of shaping the cooled nerve conduit by cutting.

9. The method for preparing a porous nerve conduit containing cells of claim 5, wherein the container is formed of a transparent material so that the infiltration of the polymer material for the nerve conduit can be checked visually.

10. The method for preparing a porous nerve conduit containing cells of claim 5, wherein the application of vacuum is repeated multiple times.

11. The method for preparing a porous nerve conduit containing cells of claim 1, wherein the cells of the step e) are nerve cells.

12. The method for preparing a porous nerve conduit containing cells of claim 11, wherein the nerve cells are one or more selected from a group comprising of Schwann cells, astrocyte and oligodendrocytes.

13. The method for preparing a porous nerve conduit containing cells of claim 1, wherein a flow rate of the culture medium of the step f) or the step g) is 30-60 μL/min.

14. The method for preparing a porous nerve conduit containing cells of claim 1, wherein the nerve conduit-inserted device allows the seeded cells to grow inside the microchannels in the nerve conduit.

* * * * *